US009144477B2

(12) United States Patent
Sokol et al.

(10) Patent No.: US 9,144,477 B2
(45) Date of Patent: Sep. 29, 2015

(54) MECHANICALLY-DRIVEN, SONIC TOOTHBRUSH SYSTEM

(71) Applicant: WATER PIK, INC., Fort Collins, CO (US)

(72) Inventors: Gary L. Sokol, Longmont, CO (US); Harold A. Luettgen, Windsor, CO (US)

(73) Assignee: WATER PIK, INC., Fort Collins, CO (US)

( * ) Notice: Subject to any disclaimer, the term of this patent is extended or adjusted under 35 U.S.C. 154(b) by 0 days.

(21) Appl. No.: 14/581,385

(22) Filed: Dec. 23, 2014

(65) Prior Publication Data

US 2015/0107035 A1    Apr. 23, 2015

Related U.S. Application Data

(63) Continuation of application No. 13/462,614, filed on May 2, 2012, now Pat. No. 8,943,634.

(60) Provisional application No. 61/481,357, filed on May 2, 2011.

(51) Int. Cl.
*A61C 17/34* (2006.01)
*A61C 17/26* (2006.01)
*A61C 17/20* (2006.01)

(52) U.S. Cl.
CPC .............. *A61C 17/26* (2013.01); *A61C 17/20* (2013.01); *A61C 17/3418* (2013.01); *A61C 17/3481* (2013.01)

(58) Field of Classification Search
CPC ........... A61C 17/3481; A61C 17/3418; A61C 17/26; A61C 17/20

USPC ............ 15/22.1, 28, 167.1; 310/68 B, 79, 81; 433/25, 86, 103, 114, 118, 119, 216; 318/119, 139; 601/142
See application file for complete search history.

(56) References Cited

U.S. PATENT DOCUMENTS

| 669,402 A | 3/1901 | Rose |
| 684,951 A | 10/1901 | Rothkranz |
| 914,501 A | 3/1909 | McEachern |
| 933,718 A | 9/1909 | Mahoney |

(Continued)

FOREIGN PATENT DOCUMENTS

| CH | 435553 | 10/1967 |
| CH | 609238 | 2/1979 |

(Continued)

OTHER PUBLICATIONS

Sonex International: Brushing with the Ultima—The World's Only Dual-Frequency Ultrasonic Toothbrush, Jul. 28, 1999, published at Sonipic.com.

(Continued)

*Primary Examiner* — Shay Karls
(74) *Attorney, Agent, or Firm* — Dorsey & Whitney LLP

(57) ABSTRACT

A sonic toothbrush system includes an electric motor, a brush shaft, and a drive assembly. The electric motor includes a drive shaft. When the electric motor is caused to operate, the drive shaft continuously rotates until the motor is caused to stop. The drive assembly is coupled between the drive shaft and the brush shaft. The drive assembly is configured to convert the rotation of the drive shaft into sonic oscillation of a toothbrush head supported on an end of the brush shaft.

16 Claims, 15 Drawing Sheets

(56) References Cited

U.S. PATENT DOCUMENTS

| | | |
|---|---|---|
| 958,371 A | 5/1910 | Danek |
| 1,018,927 A | 2/1912 | Sarrazin |
| 1,033,819 A | 7/1912 | McMann |
| 1,059,426 A | 4/1913 | Barnes |
| D45,199 S | 2/1914 | McDonagh et al. |
| D45,572 S | 4/1914 | Sarrazin |
| 1,128,139 A | 2/1915 | Hoffman |
| D49,472 S | 8/1916 | Dierke |
| 1,251,250 A | 12/1917 | Libby |
| 1,268,544 A | 6/1918 | Cates |
| 1,278,225 A | 9/1918 | Schamberg |
| 1,296,067 A | 3/1919 | Fuller |
| D53,453 S | 7/1919 | Lloyd |
| 1,313,490 A | 8/1919 | Larson |
| 1,337,173 A | 4/1920 | White |
| 1,355,037 A | 10/1920 | Dziuk |
| D57,327 S | 3/1921 | Gibson |
| 1,382,681 A | 6/1921 | Segal |
| 1,424,879 A | 8/1922 | Carlstedt |
| 1,440,785 A | 1/1923 | Levis |
| 1,456,535 A | 5/1923 | Cartwright |
| 1,488,214 A | 3/1924 | Mason |
| 1,494,448 A | 5/1924 | Sookne |
| 1,497,495 A | 6/1924 | Fincke |
| 1,517,320 A | 12/1924 | Stoddart |
| 1,527,853 A | 2/1925 | Ferdon |
| 1,588,785 A | 6/1926 | Van Sant |
| 1,639,880 A | 8/1927 | Butler |
| 1,657,450 A | 1/1928 | Barnes |
| 1,676,703 A | 7/1928 | Nuyts |
| 1,696,835 A | 12/1928 | Burnett |
| 1,703,642 A | 2/1929 | Sticht |
| 1,794,711 A | 3/1931 | Jacobs |
| 1,796,641 A | 3/1931 | Zimmerman et al. |
| 1,800,993 A | 4/1931 | Funk |
| 1,832,519 A | 11/1931 | Wheat et al. |
| 1,880,617 A | 10/1932 | White |
| 1,916,641 A | 7/1933 | Seeliger |
| 1,927,365 A | 9/1933 | Frolio |
| 1,943,225 A | 1/1934 | McIntyre |
| 1,992,770 A | 2/1935 | Rathbun |
| 2,016,597 A | 10/1935 | Drake |
| 2,016,644 A | 10/1935 | Luball |
| 2,042,239 A | 5/1936 | Planding |
| 2,044,863 A | 6/1936 | Sticht |
| D101,080 S | 9/1936 | Cosad |
| 2,114,947 A | 4/1938 | Warsaw |
| D113,743 S | 3/1939 | Kahn |
| D113,744 S | 3/1939 | Kahn |
| 2,158,738 A | 5/1939 | Baker et al. |
| 2,168,964 A | 8/1939 | Strasser |
| 2,206,726 A | 7/1940 | Lasater |
| 2,209,173 A | 7/1940 | Russell |
| 2,218,072 A | 10/1940 | Runnels |
| 2,226,663 A | 12/1940 | Hill et al. |
| 2,244,098 A | 6/1941 | Busick |
| 2,246,523 A | 6/1941 | Kulik |
| 2,273,717 A | 2/1942 | Millard et al. |
| 2,278,365 A | 3/1942 | Daniels |
| 2,279,355 A | 4/1942 | Wilensky |
| 2,282,700 A | 5/1942 | Bobbroff |
| 2,312,828 A | 3/1943 | Adamsson |
| D136,156 S | 8/1943 | Fuller |
| D139,532 S | 11/1944 | Trecek |
| D141,350 S | 5/1945 | Alexander et al. |
| D144,163 S | 3/1946 | Dolnick |
| 2,401,186 A | 5/1946 | Price |
| 2,405,029 A | 7/1946 | Gallanty et al. |
| D146,271 S | 1/1947 | Stavely |
| 2,414,775 A | 1/1947 | Stavely |
| 2,429,740 A | 10/1947 | Aufsesser |
| 2,450,635 A | 10/1948 | Dembenski |
| D154,598 S | 7/1949 | Gass |
| D155,668 S | 10/1949 | Zandberg et al. |
| D157,669 S | 3/1950 | Graves, Jr. |
| D160,101 S | 9/1950 | MacDonald |
| 2,533,345 A | 12/1950 | Bennett |
| 2,543,999 A | 3/1951 | Voss |
| D163,707 S | 6/1951 | Pifer |
| 2,558,332 A | 6/1951 | Artale |
| 2,567,080 A | 9/1951 | Pifer |
| 2,577,597 A | 12/1951 | Wright et al. |
| 2,583,750 A | 1/1952 | Runnels |
| 2,598,275 A | 5/1952 | Lakin |
| 2,618,003 A | 11/1952 | Robey |
| D169,131 S | 3/1953 | Fay |
| 2,651,068 A | 9/1953 | Seko |
| D170,680 S | 10/1953 | Del Mas |
| D172,693 S | 7/1954 | Wibbelsman et al. |
| D173,616 S | 12/1954 | Hernandez |
| 2,705,335 A | 4/1955 | Glassman et al. |
| 2,709,227 A | 5/1955 | Foley et al. |
| 2,722,703 A | 11/1955 | Green |
| 2,728,928 A | 1/1956 | Beeren |
| 2,734,139 A | 2/1956 | Murphy |
| 2,806,235 A | 9/1957 | Carstairs et al. |
| 2,819,482 A | 1/1958 | Applegate |
| 2,868,215 A | 1/1959 | Mechem |
| 2,875,458 A | 3/1959 | Tsuda |
| 2,917,758 A | 12/1959 | Held et al. |
| 2,931,371 A | 4/1960 | Petitta |
| 2,946,072 A | 7/1960 | Filler et al. |
| 2,962,033 A | 11/1960 | Lew |
| 2,977,614 A | 4/1961 | Demanuele |
| 2,977,682 A | 4/1961 | Flatray |
| 3,103,027 A | 9/1963 | Birch |
| 3,104,405 A | 9/1963 | Perrinjaquet |
| 3,106,216 A | 10/1963 | Kirby |
| D197,048 S | 12/1963 | Troy |
| D197,208 S | 12/1963 | Cassidy et al. |
| 3,143,697 A | 8/1964 | Springer |
| 3,145,404 A | 8/1964 | Fiedler |
| D199,560 S | 11/1964 | Thompson |
| D199,893 S | 12/1964 | Bond et al. |
| 3,159,859 A | 12/1964 | Rasmussen |
| 3,160,902 A | 12/1964 | Aymar |
| 3,168,834 A | 2/1965 | Smithson |
| 3,181,189 A | 5/1965 | Leyden |
| 3,183,538 A | 5/1965 | Hubner |
| 3,195,537 A | 7/1965 | Blasi |
| D202,873 S | 11/1965 | Husted |
| 3,220,039 A | 11/1965 | Dayton et al. |
| 3,229,318 A | 1/1966 | Clemens |
| 3,230,562 A | 1/1966 | Birch |
| D204,127 S | 3/1966 | Syvertson |
| 3,258,805 A | 7/1966 | Rossnan |
| 3,270,416 A | 9/1966 | Massa |
| 3,278,963 A | 10/1966 | Bond |
| 3,289,681 A | 12/1966 | Chambers |
| 3,311,116 A | 3/1967 | Foster |
| 3,316,576 A | 5/1967 | Urbrush |
| 3,335,443 A | 8/1967 | Parisi et al. |
| 3,346,748 A | 10/1967 | McNair |
| 3,358,309 A | 12/1967 | Richardson |
| 3,358,314 A | 12/1967 | Matibag |
| 3,359,588 A | 12/1967 | Kobler |
| 3,364,576 A | 1/1968 | Kern, Jr. |
| D210,066 S | 2/1968 | Johnson |
| 3,369,265 A | 2/1968 | Halberstadt et al. |
| 3,371,260 A | 2/1968 | Jackson et al. |
| D210,349 S | 3/1968 | Boldt |
| 3,375,820 A | 4/1968 | Kuris et al. |
| D212,208 S | 9/1968 | Rogers |
| 3,418,552 A | 12/1968 | Holmes |
| 3,421,524 A | 1/1969 | Waters |
| 3,430,279 A | 3/1969 | Hintze |
| 3,463,994 A | 8/1969 | Spohr |
| 3,466,689 A | 9/1969 | Aurelio et al. |
| 3,472,045 A | 10/1969 | Nelsen et al. |
| 3,472,247 A | 10/1969 | Borsum et al. |
| 3,474,799 A | 10/1969 | Cappello |
| 3,509,874 A | 5/1970 | Stillman |
| 3,535,726 A | 10/1970 | Sawyer |
| 3,536,065 A | 10/1970 | Moret |

(56) References Cited

U.S. PATENT DOCUMENTS

| | | |
|---|---|---|
| 3,538,359 A | 11/1970 | Barowski |
| 3,552,022 A | 1/1971 | Axelsson |
| 3,559,292 A | 2/1971 | Weissman |
| 3,563,233 A | 2/1971 | Bodine |
| 3,588,936 A | 6/1971 | Duve |
| 3,590,814 A | 7/1971 | Bennett et al. |
| D221,823 S | 9/1971 | Cook |
| 3,608,548 A | 9/1971 | Lewis |
| 3,642,344 A | 2/1972 | Corker |
| 3,651,576 A | 3/1972 | Massa |
| 3,660,902 A | 5/1972 | Axelsson |
| 3,667,483 A | 6/1972 | McCabe |
| 3,672,378 A | 6/1972 | Silverman |
| 3,676,218 A | 7/1972 | Sawyer |
| 3,685,080 A | 8/1972 | Hubner |
| 3,722,020 A | 3/1973 | Hills |
| 3,742,549 A | 7/1973 | Scopp et al. |
| 3,759,274 A | 9/1973 | Warner |
| 3,760,799 A | 9/1973 | Crowson |
| 3,792,504 A | 2/1974 | Smith |
| 3,809,977 A | 5/1974 | Balamuth et al. |
| 3,831,611 A | 8/1974 | Hendricks |
| 3,840,932 A | 10/1974 | Balamuth et al. |
| 3,847,167 A | 11/1974 | Brien |
| 3,851,984 A | 12/1974 | Crippa |
| D234,518 S | 3/1975 | Gerlich |
| 3,882,364 A | 5/1975 | Wright et al. |
| 3,902,510 A | 9/1975 | Roth |
| 3,903,601 A | 9/1975 | Anderson et al. |
| 3,939,599 A | 2/1976 | Henry et al. |
| 3,967,617 A | 7/1976 | Krolik |
| 3,973,558 A | 8/1976 | Stouffer et al. |
| 3,978,852 A | 9/1976 | Annoni |
| 3,980,906 A | 9/1976 | Kuris et al. |
| 4,004,344 A | 1/1977 | Gold et al. |
| 4,005,722 A | 2/1977 | Bragg |
| 4,008,728 A | 2/1977 | Sanchez |
| 4,010,509 A | 3/1977 | Huish |
| 4,014,354 A | 3/1977 | Garrett |
| 4,019,522 A | 4/1977 | Elbreder |
| 4,033,008 A | 7/1977 | Warren et al. |
| 4,048,723 A | 9/1977 | Thorup |
| 4,051,571 A | 10/1977 | Ayers |
| 4,064,883 A | 12/1977 | Oldham |
| 4,133,339 A | 1/1979 | Naslund |
| 4,141,352 A | 2/1979 | Ebner et al. |
| 4,156,620 A | 5/1979 | Clemens |
| 4,177,434 A | 12/1979 | Ida |
| D254,162 S | 2/1980 | Barker |
| 4,192,035 A | 3/1980 | Kuris |
| 4,203,431 A | 5/1980 | Abura et al. |
| 4,205,664 A | 6/1980 | Baccialon |
| 4,219,619 A | 8/1980 | Zarow |
| 4,235,253 A | 11/1980 | Moore |
| 4,245,658 A | 1/1981 | Lecouturier |
| RE30,536 E | 3/1981 | Perdreaux, Jr. |
| 4,255,693 A | 3/1981 | Keidl |
| 4,265,257 A | 5/1981 | Salyer |
| 4,268,933 A | 5/1981 | Papas |
| 4,271,382 A | 6/1981 | Maeda et al. |
| 4,271,384 A | 6/1981 | Beling et al. |
| 4,271,854 A | 6/1981 | Bengtsson |
| 4,275,363 A | 6/1981 | Mishiro et al. |
| 4,288,883 A | 9/1981 | Dolinsky |
| 4,289,486 A | 9/1981 | Sargeant |
| 4,303,064 A | 12/1981 | Buffa |
| 4,307,740 A | 12/1981 | Florindez et al. |
| 4,319,377 A | 3/1982 | Tarrson et al. |
| 4,319,595 A | 3/1982 | Ulrich |
| 4,326,547 A | 4/1982 | Verplank |
| 4,326,548 A | 4/1982 | Wagner |
| 4,326,549 A | 4/1982 | Hinding |
| 4,331,422 A | 5/1982 | Heyman |
| 4,333,197 A | 6/1982 | Kuris |
| 4,336,622 A | 6/1982 | Teague, Jr. et al. |
| D265,515 S | 7/1982 | Levine |
| 4,338,957 A | 7/1982 | Meibauer |
| D265,698 S | 8/1982 | Roth |
| 4,346,492 A | 8/1982 | Solow |
| 4,347,839 A | 9/1982 | Youngclaus, Jr. |
| 4,353,141 A | 10/1982 | Teague, Jr. et al. |
| 4,356,585 A | 11/1982 | Protell et al. |
| 4,381,478 A | 4/1983 | Saijo et al. |
| 4,395,665 A | 7/1983 | Buchas |
| 4,397,327 A | 8/1983 | Hadary |
| D270,972 S | 10/1983 | Rosofsky |
| D272,565 S | 2/1984 | Levine |
| D272,680 S | 2/1984 | Stocchi |
| 4,429,997 A | 2/1984 | Matthews |
| 4,432,729 A | 2/1984 | Fattaleh |
| 4,434,806 A | 3/1984 | Givens |
| 4,442,830 A | 4/1984 | Markau |
| D274,018 S | 5/1984 | Usui |
| 4,450,599 A | 5/1984 | Scheller et al. |
| 4,455,704 A | 6/1984 | Williams |
| 4,458,702 A | 7/1984 | Grollimund |
| 4,488,327 A | 12/1984 | Snider |
| 4,490,114 A | 12/1984 | Kleesattel |
| 4,505,678 A | 3/1985 | Andersson |
| 4,517,701 A | 5/1985 | Stanford, Jr. |
| 4,519,111 A | 5/1985 | Cavazza |
| 4,522,355 A | 6/1985 | Moran |
| 4,522,595 A | 6/1985 | Selvidge |
| 4,543,679 A | 10/1985 | Rosofsky et al. |
| D281,202 S | 11/1985 | Thompson |
| 4,562,413 A | 12/1985 | Mishiro et al. |
| 4,564,794 A | 1/1986 | Kilen et al. |
| 4,571,768 A | 2/1986 | Kawashima |
| 4,576,190 A | 3/1986 | Youssef |
| 4,577,649 A | 3/1986 | Shimenkov |
| 4,578,033 A | 3/1986 | Mossle et al. |
| D283,374 S | 4/1986 | Cheuk-Yiu |
| 4,585,415 A | 4/1986 | Hommann |
| 4,586,521 A | 5/1986 | Urso |
| D284,236 S | 6/1986 | Collet |
| D284,528 S | 7/1986 | Jurado |
| 4,603,448 A | 8/1986 | Middleton et al. |
| 4,605,025 A | 8/1986 | McSpadden |
| 4,608,019 A | 8/1986 | Kumabe et al. |
| 4,610,043 A | 9/1986 | Vezjak |
| 4,617,695 A | 10/1986 | Amos et al. |
| 4,617,718 A | 10/1986 | Andersson |
| D287,073 S | 12/1986 | Thompson |
| 4,634,376 A | 1/1987 | Mossle et al. |
| 4,644,937 A | 2/1987 | Hommann |
| 4,655,198 A | 4/1987 | Hommann |
| 4,672,706 A | 6/1987 | Hill |
| D292,448 S | 10/1987 | Vianello |
| 4,698,869 A | 10/1987 | Mierau et al. |
| 4,706,322 A | 11/1987 | Nicolas |
| 4,706,695 A | 11/1987 | Urso |
| D294,885 S | 3/1988 | Mollenhoff |
| 4,729,142 A | 3/1988 | Yoshioka |
| D297,467 S | 8/1988 | McCann |
| 4,766,630 A | 8/1988 | Hegemann |
| 4,776,054 A | 10/1988 | Rauch |
| 4,787,847 A | 11/1988 | Martin et al. |
| 4,791,940 A | 12/1988 | Hirshfeld et al. |
| 4,800,608 A | 1/1989 | Key |
| 4,802,255 A | 2/1989 | Breuer et al. |
| 4,811,445 A | 3/1989 | Lagieski et al. |
| 4,820,153 A | 4/1989 | Romhild et al. |
| 4,820,154 A | 4/1989 | Romhild et al. |
| 4,827,550 A | 5/1989 | Graham et al. |
| 4,827,552 A | 5/1989 | Bojar et al. |
| 4,832,063 A | 5/1989 | Smole |
| D301,770 S | 6/1989 | Bethany |
| 4,844,104 A | 7/1989 | Martin |
| 4,845,795 A | 7/1989 | Crawford et al. |
| 4,856,133 A | 8/1989 | Sanchez |
| 4,864,676 A | 9/1989 | Schaiper |
| D303,876 S | 10/1989 | Clemens et al. |
| 4,871,396 A | 10/1989 | Tsujita et al. |
| 4,873,496 A | 10/1989 | Ohgihara et al. |

(56) References Cited

U.S. PATENT DOCUMENTS

| | | |
|---|---|---|
| 4,875,265 A | 10/1989 | Yoshida |
| 4,877,934 A | 10/1989 | Spinello |
| 4,879,781 A | 11/1989 | Desimone |
| 4,880,382 A | 11/1989 | Moret et al. |
| 4,887,052 A | 12/1989 | Murakami et al. |
| 4,892,191 A | 1/1990 | Nakamara |
| 4,908,902 A | 3/1990 | McNab et al. |
| 4,913,133 A | 4/1990 | Tichy |
| 4,913,176 A | 4/1990 | DeNiro |
| 4,922,936 A | 5/1990 | Buzzi et al. |
| D308,765 S | 6/1990 | Johnson |
| 4,974,278 A | 12/1990 | Hommann |
| 4,984,173 A | 1/1991 | Imam et al. |
| 4,989,287 A | 2/1991 | Scherer |
| 4,991,249 A | 2/1991 | Suroff |
| 4,995,403 A | 2/1991 | Beckman et al. |
| 5,000,684 A | 3/1991 | Odrich |
| 5,002,487 A | 3/1991 | Tichy |
| 5,007,127 A | 4/1991 | Paolo |
| 5,016,660 A | 5/1991 | Boggs |
| 5,020,179 A | 6/1991 | Scherer |
| 5,033,150 A | 7/1991 | Gross et al. |
| D318,918 S | 8/1991 | Hartwein |
| D319,363 S | 8/1991 | Uemura et al. |
| 5,046,212 A | 9/1991 | O'Conke |
| 5,050,625 A | 9/1991 | Siekmann |
| 5,054,149 A | 10/1991 | Si-Hoe et al. |
| D321,285 S | 11/1991 | Hirabayashi |
| 5,062,797 A | 11/1991 | Gonser |
| 5,067,223 A | 11/1991 | Bruno |
| D321,986 S | 12/1991 | Snyder et al. |
| 5,068,939 A | 12/1991 | Holland |
| 5,069,233 A | 12/1991 | Ritter |
| 5,069,621 A | 12/1991 | Paradis |
| 5,071,348 A | 12/1991 | Woog |
| 5,072,477 A | 12/1991 | Pai |
| 5,072,482 A | 12/1991 | Bojar et al. |
| 5,077,855 A | 1/1992 | Ambasz |
| 5,085,236 A | 2/1992 | Odneal et al. |
| 5,088,145 A | 2/1992 | Whitefield |
| D324,957 S | 3/1992 | Piano |
| 5,094,256 A | 3/1992 | Barth |
| 5,095,470 A | 3/1992 | Oka et al. |
| 5,100,321 A | 3/1992 | Coss et al. |
| 5,120,225 A | 6/1992 | Amit |
| 5,123,841 A | 6/1992 | Millner |
| 5,125,837 A | 6/1992 | Warrin et al. |
| 5,133,661 A | 7/1992 | Euvrard |
| 5,138,733 A | 8/1992 | Bock |
| 5,145,369 A | 9/1992 | Lustig et al. |
| 5,146,643 A | 9/1992 | Bojar et al. |
| 5,150,492 A | 9/1992 | Suroff |
| 5,151,030 A | 9/1992 | Comeaux |
| D330,116 S | 10/1992 | Crawford et al. |
| D330,286 S | 10/1992 | Curtis et al. |
| D330,458 S | 10/1992 | Curtis et al. |
| 5,152,394 A | 10/1992 | Hughes |
| 5,163,375 A | 11/1992 | Withers et al. |
| 5,165,131 A | 11/1992 | Staar |
| 5,167,193 A | 12/1992 | Withers et al. |
| 5,169,313 A | 12/1992 | Kline |
| 5,170,809 A | 12/1992 | Imai et al. |
| 5,174,314 A | 12/1992 | Charatan |
| 5,176,157 A | 1/1993 | Mazza |
| 5,177,826 A | 1/1993 | Vrignaud et al. |
| 5,180,363 A | 1/1993 | Idemoto et al. |
| D332,873 S | 2/1993 | Hall |
| 5,183,063 A | 2/1993 | Ringle et al. |
| 5,183,156 A | 2/1993 | Bruno |
| 5,184,368 A | 2/1993 | Holland |
| 5,184,632 A | 2/1993 | Gross et al. |
| 5,186,191 A | 2/1993 | Loubier |
| 5,188,133 A | 2/1993 | Romanus |
| 5,189,751 A | 3/1993 | Giuliani et al. |
| 5,193,678 A | 3/1993 | Janocik et al. |
| 5,198,732 A | 3/1993 | Morimoto |
| D334,472 S | 4/1993 | Curtis et al. |
| 5,201,092 A | 4/1993 | Colson |
| D335,579 S | 5/1993 | Chuang |
| 5,207,773 A | 5/1993 | Henderson |
| 5,213,434 A | 5/1993 | Hahn |
| 5,214,819 A | 6/1993 | Kirchner |
| 5,217,031 A | 6/1993 | Santoro |
| 5,224,500 A | 7/1993 | Stella |
| 5,226,206 A | 7/1993 | Davidovitz et al. |
| 5,236,358 A | 8/1993 | Sieffert |
| 5,245,117 A | 9/1993 | Withers et al. |
| 5,246,022 A | 9/1993 | Israel et al. |
| 5,247,716 A | 9/1993 | Bock |
| 5,253,382 A | 10/1993 | Beny |
| 5,261,430 A | 11/1993 | Mochel |
| 5,263,218 A | 11/1993 | Giuliani et al. |
| D341,943 S | 12/1993 | Si-Hoe |
| D342,160 S | 12/1993 | Curtis et al. |
| D342,161 S | 12/1993 | Curtis et al. |
| D342,162 S | 12/1993 | Curtis et al. |
| 5,267,579 A | 12/1993 | Bushberger |
| D343,064 S | 1/1994 | Reno |
| 5,279,314 A | 1/1994 | Poulos et al. |
| 5,289,604 A | 3/1994 | Kressner |
| 5,293,886 A | 3/1994 | Czapor |
| 5,294,896 A | 3/1994 | Kjellander et al. |
| D346,212 S | 4/1994 | Hosl |
| 5,299,723 A | 4/1994 | Hempel |
| 5,305,492 A | 4/1994 | Giuliani et al. |
| D346,697 S | 5/1994 | O'Conke |
| 5,309,590 A | 5/1994 | Giuliani et al. |
| 5,309,591 A | 5/1994 | Hägele et al. |
| 5,311,632 A | 5/1994 | Center |
| 5,311,633 A | 5/1994 | Herzog et al. |
| 5,315,731 A | 5/1994 | Millar |
| D347,943 S | 6/1994 | Perry |
| 5,323,796 A | 6/1994 | Urso |
| 5,335,389 A | 8/1994 | Curtis et al. |
| 5,337,435 A | 8/1994 | Krasner et al. |
| 5,339,482 A | 8/1994 | Desimone et al. |
| 5,341,534 A | 8/1994 | Serbinski et al. |
| 5,341,537 A | 8/1994 | Curtis et al. |
| 5,351,358 A | 10/1994 | Larrimore |
| 5,353,460 A | 10/1994 | Bauman |
| 5,354,246 A | 10/1994 | Gotman |
| 5,355,638 A | 10/1994 | Hoffman |
| 5,358,328 A | 10/1994 | Inoue et al. |
| D352,396 S | 11/1994 | Curtis et al. |
| D352,829 S | 11/1994 | Perry |
| 5,359,747 A | 11/1994 | Amakasu |
| 5,365,627 A | 11/1994 | Jousson et al. |
| D353,490 S | 12/1994 | Hartwein |
| 5,369,831 A | 12/1994 | Bock |
| 5,371,915 A | 12/1994 | Key |
| 5,373,602 A | 12/1994 | Bang |
| D354,168 S | 1/1995 | Hartwein |
| 5,378,153 A | 1/1995 | Giuliani et al. |
| 5,383,242 A | 1/1995 | Bigler et al. |
| 5,392,483 A | 2/1995 | Heinzelman et al. |
| 5,393,229 A | 2/1995 | Ram |
| 5,396,678 A | 3/1995 | Bredall et al. |
| 5,398,368 A | 3/1995 | Elder |
| 5,400,811 A | 3/1995 | Meibauer |
| 5,404,608 A | 4/1995 | Hommann |
| 5,406,664 A | 4/1995 | Hukuba |
| 5,406,965 A | 4/1995 | Levine |
| D358,486 S | 5/1995 | Loew |
| D358,713 S | 5/1995 | Perry |
| D358,801 S | 5/1995 | Vos |
| 5,411,041 A | 5/1995 | Ritter |
| 5,412,827 A | 5/1995 | Muller et al. |
| 5,416,942 A | 5/1995 | Baldacci et al. |
| 5,419,346 A | 5/1995 | Tipp |
| 5,419,703 A | 5/1995 | Warrin et al. |
| D358,938 S | 6/1995 | Schneider et al. |
| 5,421,726 A | 6/1995 | Okada |
| 5,435,032 A | 7/1995 | McDougall |
| 5,438,726 A | 8/1995 | Leite |

(56) References Cited

U.S. PATENT DOCUMENTS

| | | | |
|---|---|---|---|
| 5,446,940 A | 9/1995 | Curtis et al. | |
| D363,605 S | 10/1995 | Kou et al. | |
| 5,459,898 A | 10/1995 | Bacolot | |
| 5,461,744 A | 10/1995 | Merbach | |
| 5,467,494 A | 11/1995 | Muller et al. | |
| 5,467,495 A | 11/1995 | Boland et al. | |
| 5,482,466 A | 1/1996 | Haynes | |
| 5,484,281 A | 1/1996 | Renow et al. | |
| 5,496,256 A | 3/1996 | Bock et al. | |
| 5,499,420 A | 3/1996 | Boland | |
| 5,504,958 A | 4/1996 | Herzog | |
| 5,504,959 A * | 4/1996 | Yukawa et al. | 15/22.1 |
| 5,511,270 A | 4/1996 | Eliachar et al. | |
| 5,511,275 A | 4/1996 | Volpenhein et al. | |
| D370,125 S | 5/1996 | Craft et al. | |
| 5,518,012 A | 5/1996 | Dolan et al. | |
| D370,347 S | 6/1996 | Heinzelman et al. | |
| 5,529,494 A | 6/1996 | Vlacancich | |
| D371,242 S | 7/1996 | Shimatsu et al. | |
| 5,530,981 A | 7/1996 | Chen | |
| 5,544,382 A | 8/1996 | Giuliani et al. | |
| 5,545,968 A | 8/1996 | Hilfinger et al. | |
| 5,546,624 A | 8/1996 | Bock | |
| 5,546,626 A | 8/1996 | Chung | |
| 5,561,881 A | 10/1996 | Klinger et al. | |
| D375,841 S | 11/1996 | Serbinski | |
| 5,573,020 A | 11/1996 | Robinson | |
| 5,577,285 A | 11/1996 | Drossler | |
| D376,695 S | 12/1996 | Tveras | |
| 5,579,786 A | 12/1996 | Wolk et al. | |
| 5,584,690 A | 12/1996 | Maassarani | |
| 5,588,452 A | 12/1996 | Peck | |
| 5,606,984 A | 3/1997 | Gao | |
| 5,609,170 A | 3/1997 | Roth | |
| 5,613,258 A | 3/1997 | Hilfinger et al. | |
| 5,613,259 A | 3/1997 | Craft et al. | |
| 5,617,601 A | 4/1997 | McDougall | |
| 5,617,602 A | 4/1997 | Okada | |
| 5,618,275 A | 4/1997 | Bock | |
| 5,619,766 A | 4/1997 | Zhadanov et al. | |
| 5,623,746 A | 4/1997 | Ichiro | |
| 5,625,916 A | 5/1997 | McDougall | |
| 5,628,082 A | 5/1997 | Moskovich | |
| D380,903 S | 7/1997 | Moskovich | |
| D381,468 S | 7/1997 | Dolan et al. | |
| 5,651,157 A | 7/1997 | Hahn | |
| D382,407 S | 8/1997 | Craft et al. | |
| 5,652,990 A | 8/1997 | Driesen et al. | |
| 5,653,591 A | 8/1997 | Loge | |
| 5,678,274 A | 10/1997 | Liu | |
| 5,678,578 A | 10/1997 | Kossak et al. | |
| D386,314 S | 11/1997 | Moskovich | |
| 5,687,446 A | 11/1997 | Chen et al. | |
| 5,697,117 A | 12/1997 | Craft | |
| 5,700,146 A | 12/1997 | Kucar | |
| RE35,712 E | 1/1998 | Murayama | |
| 5,704,087 A | 1/1998 | Strub | |
| 5,709,233 A | 1/1998 | Boland et al. | |
| 5,718,667 A | 2/1998 | Sugimoto et al. | |
| 5,732,433 A | 3/1998 | Göcking et al. | |
| 5,735,011 A | 4/1998 | Asher | |
| 5,738,575 A | 4/1998 | Bock | |
| 5,742,972 A | 4/1998 | Bredall et al. | |
| 5,749,380 A | 5/1998 | Zebuhr | |
| 5,762,078 A | 6/1998 | Zebuhr | |
| 5,775,346 A | 7/1998 | Szyszkowski | |
| 5,784,742 A | 7/1998 | Giuliani et al. | |
| 5,784,743 A | 7/1998 | Shek | |
| D397,251 S | 8/1998 | Eguchi et al. | |
| D397,254 S | 8/1998 | Moskovich | |
| 5,787,908 A | 8/1998 | Robinson | |
| 5,794,295 A | 8/1998 | Shen | |
| 5,815,872 A | 10/1998 | Meginniss, III et al. | |
| 5,816,271 A | 10/1998 | Urso | |
| 5,822,821 A | 10/1998 | Sham | |
| 5,827,064 A | 10/1998 | Bock | |
| D400,713 S | 11/1998 | Solanki | |
| 5,836,030 A | 11/1998 | Hazeu et al. | |
| 5,842,244 A | 12/1998 | Hilfinger et al. | |
| 5,850,655 A | 12/1998 | Göcking et al. | |
| 5,851,514 A | 12/1998 | Hassan et al. | |
| D403,511 S | 1/1999 | Serbinski | |
| 5,855,216 A | 1/1999 | Robinson | |
| 5,862,558 A | 1/1999 | Hilfinger et al. | |
| 5,864,911 A | 2/1999 | Arnoux | |
| 5,864,915 A | 2/1999 | Ra | |
| 5,867,856 A | 2/1999 | Herzog | |
| 5,875,797 A | 3/1999 | Chiang et al. | |
| 5,893,175 A | 4/1999 | Cooper | |
| 5,896,614 A | 4/1999 | Flewitt | |
| 5,896,615 A | 4/1999 | Zaksenberg | |
| 5,899,693 A | 5/1999 | Himeno et al. | |
| 5,900,230 A | 5/1999 | Cutler | |
| 5,901,397 A | 5/1999 | Hafele et al. | |
| D410,787 S | 6/1999 | Barre et al. | |
| 5,908,038 A | 6/1999 | Bennett | |
| D411,769 S | 7/1999 | Wright | |
| 5,921,254 A | 7/1999 | Carlucci et al. | |
| 5,927,300 A | 7/1999 | Boland et al. | |
| 5,927,976 A | 7/1999 | Wu | |
| 5,930,858 A | 8/1999 | Jung | |
| 5,931,170 A | 8/1999 | Wu | |
| 5,934,908 A | 8/1999 | Woog et al. | |
| 5,943,723 A | 8/1999 | Hilfinger et al. | |
| 5,944,033 A | 8/1999 | Robinson | |
| D413,694 S | 9/1999 | Bennett | |
| D414,937 S | 10/1999 | Cornu et al. | |
| D414,939 S | 10/1999 | Pedro, Jr. et al. | |
| 5,974,613 A | 11/1999 | Herzog | |
| 5,974,615 A | 11/1999 | Schwarz-Hartmann et al. | |
| 5,980,541 A | 11/1999 | Tenzer | |
| 5,987,681 A | 11/1999 | Hahn et al. | |
| 5,991,957 A | 11/1999 | Watanabe | |
| D417,960 S | 12/1999 | Moskovich et al. | |
| 6,000,083 A | 12/1999 | Blaustein et al. | |
| 6,009,589 A | 1/2000 | Driesen et al. | |
| 6,021,538 A | 2/2000 | Kressner et al. | |
| 6,026,828 A | 2/2000 | Altshuler | |
| 6,032,313 A | 3/2000 | Tsang | |
| 6,035,476 A | 3/2000 | Underwood et al. | |
| 6,047,711 A | 4/2000 | Wagner | |
| 6,050,818 A | 4/2000 | Boland et al. | |
| RE36,699 E | 5/2000 | Murayama | |
| D423,784 S | 5/2000 | Joulin | |
| 6,065,176 A | 5/2000 | Watanabe et al. | |
| 6,081,957 A | 7/2000 | Webb | |
| 6,092,252 A | 7/2000 | Fischer et al. | |
| 6,095,811 A | 8/2000 | Stearns | |
| 6,102,700 A | 8/2000 | Haczek et al. | |
| 6,106,294 A | 8/2000 | Daniel | |
| 6,138,310 A | 10/2000 | Porper et al. | |
| 6,140,723 A | 10/2000 | Matsui et al. | |
| 6,148,462 A | 11/2000 | Zseng | |
| D434,563 S | 12/2000 | Lim et al. | |
| 6,154,912 A | 12/2000 | Li | |
| 6,162,202 A | 12/2000 | Sicurelli et al. | |
| 6,165,131 A | 12/2000 | Cuce' et al. | |
| D437,090 S | 1/2001 | Lang et al. | |
| D437,091 S | 1/2001 | Lang et al. | |
| 6,178,579 B1 | 1/2001 | Blaustein et al. | |
| D437,663 S | 2/2001 | Lang et al. | |
| D437,976 S | 2/2001 | Narayanan et al. | |
| D437,977 S | 2/2001 | Lang et al. | |
| D438,306 S | 2/2001 | Narayanan | |
| 6,183,254 B1 | 2/2001 | Cohen | |
| 6,195,828 B1 | 3/2001 | Fritsch | |
| 6,202,242 B1 | 3/2001 | Salmon et al. | |
| 6,203,320 B1 | 3/2001 | Williams et al. | |
| 6,220,857 B1 | 4/2001 | Abels | |
| 6,230,354 B1 | 5/2001 | Sproat | |
| 6,230,717 B1 | 5/2001 | Marx et al. | |
| 6,233,773 B1 | 5/2001 | Karge et al. | |
| 6,237,178 B1 | 5/2001 | Krammer et al. | |
| D444,629 S | 7/2001 | Etter et al. | |

(56) References Cited

U.S. PATENT DOCUMENTS

| | | |
|---|---|---|
| 6,253,404 B1 | 7/2001 | Boland et al. |
| 6,267,593 B1 | 7/2001 | Haczek et al. |
| 6,299,444 B1 | 10/2001 | Cohen |
| 6,308,358 B2 | 10/2001 | Gruber et al. |
| 6,308,359 B2 | 10/2001 | Fritsch et al. |
| 6,341,400 B1 | 1/2002 | Kobayashi et al. |
| 6,343,396 B1 | 2/2002 | Simovitz et al. |
| 6,343,400 B1 | 2/2002 | Massholder et al. |
| 6,347,425 B1 | 2/2002 | Fattori et al. |
| 6,349,442 B1 | 2/2002 | Cohen et al. |
| 6,353,956 B1 | 3/2002 | Berge |
| 6,360,395 B2 | 3/2002 | Blaustein et al. |
| 6,360,398 B1 | 3/2002 | Wiegner et al. |
| 6,363,565 B1 | 4/2002 | Paffrath |
| 6,365,108 B1 | 4/2002 | Philyaw |
| 6,367,108 B1 | 4/2002 | Fritsch et al. |
| 6,374,448 B2 | 4/2002 | Seifert |
| 6,375,459 B1 | 4/2002 | Kamen et al. |
| 6,381,795 B1 | 5/2002 | Hofmann et al. |
| 6,401,288 B1 | 6/2002 | Porper et al. |
| 6,421,865 B1 | 7/2002 | McDougall |
| 6,421,866 B1 | 7/2002 | McDougall |
| 6,421,867 B1 | 7/2002 | Weihrauch |
| 6,422,867 B2 | 7/2002 | Lang et al. |
| 6,434,773 B1 | 8/2002 | Kuo |
| D463,627 S | 9/2002 | Lang et al. |
| 6,446,294 B1 | 9/2002 | Specht |
| 6,446,295 B1 | 9/2002 | Calabrese |
| 6,447,293 B1 | 9/2002 | Sokol et al. |
| 6,453,497 B1 | 9/2002 | Chiang et al. |
| 6,453,498 B1 | 9/2002 | Wu |
| 6,453,499 B1 | 9/2002 | Leuermann |
| 6,463,615 B1 | 10/2002 | Gruber et al. |
| 6,490,747 B1 | 12/2002 | Metwally |
| 6,497,237 B1 | 12/2002 | Ali |
| 6,510,575 B2 | 1/2003 | Calabrese |
| 6,526,994 B1 | 3/2003 | Santoro |
| 6,536,066 B2 | 3/2003 | Dickie |
| 6,564,940 B2 | 5/2003 | Blaustein et al. |
| 6,571,804 B2 | 6/2003 | Adler |
| 6,574,820 B1 | 6/2003 | DePuydt et al. |
| 6,581,233 B1 | 6/2003 | Cheng |
| 6,581,234 B2 | 6/2003 | Lee et al. |
| 6,588,042 B2 | 7/2003 | Fritsch et al. |
| 6,599,048 B2 | 7/2003 | Kuo |
| 6,609,527 B2 | 8/2003 | Brown |
| 6,609,910 B2 | 8/2003 | Narayanan |
| 6,619,299 B2 | 9/2003 | Marcon et al. |
| 6,622,333 B1 | 9/2003 | Rehkemper et al. |
| 6,647,577 B2 | 11/2003 | Tam |
| D484,311 S | 12/2003 | Cacka et al. |
| 6,654,979 B2 | 12/2003 | Calabrese |
| 6,659,674 B2 | 12/2003 | Carlucci et al. |
| 6,665,901 B2 | 12/2003 | Driesen et al. |
| 6,691,363 B2 | 2/2004 | Huen |
| 6,701,565 B2 | 3/2004 | Hafemann |
| 6,709,185 B2 | 3/2004 | Lefevre |
| 6,721,986 B2 | 4/2004 | Zhuan |
| 6,725,490 B2 | 4/2004 | Blaustein et al. |
| 6,735,803 B2 | 5/2004 | Kuo |
| 6,735,804 B2 | 5/2004 | Carlucci et al. |
| 6,739,012 B2 | 5/2004 | Grez et al. |
| 6,751,823 B2 | 6/2004 | Biro et al. |
| 6,760,945 B2 | 7/2004 | Ferber et al. |
| 6,760,946 B2 | 7/2004 | DePuydt |
| 6,766,548 B1 | 7/2004 | Lukas et al. |
| 6,766,549 B2 | 7/2004 | Klupt |
| 6,766,807 B2 | 7/2004 | Piccolo et al. |
| 6,779,126 B1 | 8/2004 | Lin et al. |
| 6,779,215 B2 | 8/2004 | Hartman et al. |
| 6,785,926 B2 | 9/2004 | Green |
| 6,785,929 B2 | 9/2004 | Fritsch et al. |
| 6,792,640 B2 | 9/2004 | Lev |
| 6,795,993 B2 | 9/2004 | Lin |
| 6,798,169 B2 | 9/2004 | Stratmann et al. |
| 6,799,346 B2 | 10/2004 | Jeng et al. |
| 6,802,097 B2 | 10/2004 | Hafliger et al. |
| 6,810,550 B1 | 11/2004 | Wuelknitz et al. |
| 6,813,793 B2 | 11/2004 | Eliav |
| 6,813,794 B2 | 11/2004 | Weng |
| 6,821,119 B2 | 11/2004 | Shortt et al. |
| 6,823,875 B2 | 11/2004 | Hotta et al. |
| 6,827,910 B2 | 12/2004 | Chen |
| 6,829,801 B2 | 12/2004 | Schutz |
| 6,832,819 B1 | 12/2004 | Weihrauch |
| D500,599 S | 1/2005 | Callaghan |
| D501,084 S | 1/2005 | Schaefer et al. |
| 6,836,917 B2 | 1/2005 | Blaustein et al. |
| 6,845,537 B2 | 1/2005 | Wong |
| 6,848,141 B2 | 2/2005 | Eliav et al. |
| 6,851,150 B2 | 2/2005 | Chiang |
| 6,851,153 B2 | 2/2005 | Lehman |
| 6,854,965 B2 | 2/2005 | Ebner et al. |
| 6,862,771 B1 | 3/2005 | Muller |
| 6,871,373 B2 | 3/2005 | Driesen et al. |
| 6,874,509 B2 | 4/2005 | Bergman |
| 6,886,207 B1 | 5/2005 | Solanki |
| 6,889,401 B2 | 5/2005 | Fattori et al. |
| 6,889,829 B2 | 5/2005 | Lev et al. |
| 6,892,412 B2 | 5/2005 | Gatzemeyer et al. |
| 6,892,413 B2 | 5/2005 | Blaustein et al. |
| 6,895,625 B2 | 5/2005 | Lev et al. |
| 6,895,629 B1 | 5/2005 | Wenzler |
| 6,902,337 B1 | 6/2005 | Kuo |
| 6,907,636 B2 | 6/2005 | Hafemann |
| 6,918,153 B2 | 7/2005 | Gruber |
| 6,920,659 B2 | 7/2005 | Cacka et al. |
| 6,920,660 B2 | 7/2005 | Lam |
| 6,928,685 B1 | 8/2005 | Blaustein et al. |
| 6,931,688 B2 | 8/2005 | Moskovich et al. |
| 6,938,293 B2 | 9/2005 | Eliav et al. |
| 6,938,294 B2 | 9/2005 | Fattori et al. |
| 6,944,901 B2 | 9/2005 | Gatzemeyer et al. |
| 6,945,397 B2 | 9/2005 | Brattesani et al. |
| 6,948,209 B2 | 9/2005 | Chan |
| 6,952,854 B2 | 10/2005 | Blaustein et al. |
| 6,952,855 B2 | 10/2005 | Lev et al. |
| 6,954,961 B2 | 10/2005 | Ferber et al. |
| 6,955,539 B2 | 10/2005 | Shortt et al. |
| 6,957,468 B2 | 10/2005 | Driesen et al. |
| 6,957,469 B2 | 10/2005 | Davies |
| 6,966,093 B2 | 11/2005 | Eliav et al. |
| 6,973,694 B2 | 12/2005 | Schutz et al. |
| 6,983,507 B2 | 1/2006 | McDougall |
| 6,988,777 B2 | 1/2006 | Pfenniger et al. |
| 6,990,706 B2 | 1/2006 | Broecker et al. |
| D515,318 S | 2/2006 | Chan et al. |
| 6,993,803 B2 | 2/2006 | Chan |
| 6,997,191 B2 | 2/2006 | Nudo, Sr. |
| 7,007,331 B2 | 3/2006 | Davics et al. |
| 7,008,225 B2 | 3/2006 | Ito et al. |
| 7,020,925 B1 | 4/2006 | Gitelis |
| 7,021,851 B1 | 4/2006 | King |
| 7,024,717 B2 | 4/2006 | Hilscher et al. |
| 7,024,718 B2 | 4/2006 | Chu |
| 7,036,180 B2 | 5/2006 | Hanlon |
| 7,055,205 B2 | 6/2006 | Aoyama |
| 7,059,334 B2 | 6/2006 | Dougan et al. |
| 7,065,821 B2 | 6/2006 | Fattori |
| RE39,185 E | 7/2006 | Noe et al. |
| 7,070,354 B1 | 7/2006 | Gutierrez-Caro |
| 7,080,980 B2 | 7/2006 | Klupt |
| 7,082,638 B2 | 8/2006 | Koh |
| 7,082,950 B2 | 8/2006 | Kossak et al. |
| 7,086,111 B2 | 8/2006 | Hilscher et al. |
| 7,089,621 B2 | 8/2006 | Hohlbein |
| 7,120,960 B2 | 10/2006 | Hilscher et al. |
| 7,122,921 B2 | 10/2006 | Hall et al. |
| 7,124,461 B2 | 10/2006 | Blaustein et al. |
| 7,124,462 B2 | 10/2006 | Lee |
| 7,128,492 B1 | 10/2006 | Thames, Jr. |
| 7,137,163 B2 | 11/2006 | Gatzemeyer et al. |
| 7,140,058 B2 | 11/2006 | Gatzemeyer et al. |
| 7,146,675 B2 | 12/2006 | Ansari et al. |

(56) References Cited

U.S. PATENT DOCUMENTS

| | | | |
|---|---|---|---|
| 7,162,764 B2 | 1/2007 | Drossler et al. |
| 7,162,767 B2 | 1/2007 | Pfenniger et al. |
| 7,168,122 B1 | 1/2007 | Riddell |
| 7,168,125 B2 | 1/2007 | Hohlbein |
| 7,174,596 B2 | 2/2007 | Fischer et al. |
| 7,175,238 B1 | 2/2007 | Barman |
| 7,181,799 B2 | 2/2007 | Gavney, Jr. et al. |
| 7,185,383 B2 | 3/2007 | Gatzemeyer et al. |
| 7,186,226 B2 | 3/2007 | Woolley |
| D540,542 S | 4/2007 | Harada |
| 7,198,487 B2 | 4/2007 | Luettgen et al. |
| 7,207,080 B2 | 4/2007 | Hilscher et al. |
| 7,210,184 B2 | 5/2007 | Eliav et al. |
| 7,213,293 B1 | 5/2007 | Schraga |
| 7,213,995 B2 | 5/2007 | Bravo-Loubriel |
| 7,217,332 B2 | 5/2007 | Brown, Jr. et al. |
| 7,222,381 B2 | 5/2007 | Kraemer |
| 7,222,382 B2 | 5/2007 | Choi et al. |
| 7,225,494 B2 | 6/2007 | Chan et al. |
| 7,228,583 B2 | 6/2007 | Chan et al. |
| 7,234,187 B2 | 6/2007 | Blaustein et al. |
| 7,234,192 B2 | 6/2007 | Barbar |
| 7,469,440 B2 | 12/2008 | Boland et al. |
| 7,554,225 B2 | 6/2009 | Kraus et al. |
| 8,032,964 B2 | 10/2011 | Farrell et al. |
| 2001/0035194 A1 | 11/2001 | Narayanan |
| 2001/0039955 A1 | 11/2001 | Winters et al. |
| 2001/0054563 A1 | 12/2001 | Lang et al. |
| 2002/0017474 A1 | 2/2002 | Blaustein et al. |
| 2002/0029988 A1 | 3/2002 | Blaustein et al. |
| 2002/0032941 A1 | 3/2002 | Blaustein et al. |
| 2002/0039720 A1 | 4/2002 | Marx et al. |
| 2002/0059685 A1 | 5/2002 | Paffrath |
| 2002/0078514 A1 | 6/2002 | Blaustein et al. |
| 2002/0084707 A1 | 7/2002 | Tang |
| 2002/0088068 A1 | 7/2002 | Levy et al. |
| 2002/0095734 A1 | 7/2002 | Wong |
| 2002/0100134 A1 | 8/2002 | Dunn et al. |
| 2002/0106607 A1 | 8/2002 | Horowitz |
| 2002/0137728 A1 | 9/2002 | Montgomery |
| 2002/0138926 A1 | 10/2002 | Brown, Jr. et al. |
| 2002/0152563 A1 | 10/2002 | Sato |
| 2002/0152564 A1 | 10/2002 | Blaustein et al. |
| 2002/0174498 A1 | 11/2002 | Li |
| 2002/0178519 A1 | 12/2002 | Zarlengo |
| 2003/0005544 A1 | 1/2003 | Felix |
| 2003/0033679 A1 | 2/2003 | Fattori et al. |
| 2003/0033680 A1 | 2/2003 | Davies et al. |
| 2003/0041396 A1 | 3/2003 | Dickie |
| 2003/0064348 A1 | 4/2003 | Sokol et al. |
| 2003/0066145 A1 | 4/2003 | Prineppi |
| 2003/0074751 A1 | 4/2003 | Wu |
| 2003/0079305 A1 | 5/2003 | Takahata et al. |
| 2003/0084525 A1 | 5/2003 | Blaustein et al. |
| 2003/0084526 A1 | 5/2003 | Brown et al. |
| 2003/0084527 A1 | 5/2003 | Brown et al. |
| 2003/0097723 A1 | 5/2003 | Li |
| 2003/0099502 A1 | 5/2003 | Lai |
| 2003/0106565 A1 | 6/2003 | Andrews |
| 2003/0140435 A1 | 7/2003 | Eliav et al. |
| 2003/0140437 A1 | 7/2003 | Eliav et al. |
| 2003/0140937 A1 | 7/2003 | Cook |
| 2003/0150474 A1 | 8/2003 | Doyscher |
| 2003/0154567 A1 | 8/2003 | Drossler et al. |
| 2003/0154568 A1 | 8/2003 | Boland et al. |
| 2003/0163881 A1 | 9/2003 | Driesen et al. |
| 2003/0163882 A1 | 9/2003 | Blaustein et al. |
| 2003/0182743 A1 | 10/2003 | Gatzemeyer et al. |
| 2003/0182746 A1 | 10/2003 | Fattori et al. |
| 2003/0192139 A1 | 10/2003 | Fattori et al. |
| 2003/0196283 A1 | 10/2003 | Eliav et al. |
| 2003/0196677 A1 | 10/2003 | Wiseman |
| 2003/0213075 A1 | 11/2003 | Hui et al. |
| 2003/0221267 A1 | 12/2003 | Chan |
| 2003/0221269 A1 | 12/2003 | Zhuan |
| 2003/0226223 A1 | 12/2003 | Chan |
| 2004/0010870 A1 | 1/2004 | McNair |
| 2004/0010871 A1 | 1/2004 | Nishinaka et al. |
| 2004/0016068 A1 | 1/2004 | Lee |
| 2004/0016069 A1 | 1/2004 | Lee |
| 2004/0034951 A1 | 2/2004 | Davies et al. |
| 2004/0045106 A1 | 3/2004 | Lam |
| 2004/0045107 A1 | 3/2004 | Egeresi |
| 2004/0049867 A1 | 3/2004 | Hui |
| 2004/0049868 A1 | 3/2004 | Ng |
| 2004/0060137 A1 | 4/2004 | Eliav |
| 2004/0063603 A1 | 4/2004 | Dave et al. |
| 2004/0068811 A1 | 4/2004 | Fulop et al. |
| 2004/0074026 A1 | 4/2004 | Blaustein et al. |
| 2004/0083566 A1 | 5/2004 | Blaustein et al. |
| 2004/0087882 A1 | 5/2004 | Roberts et al. |
| 2004/0088806 A1 | 5/2004 | DePuydt et al. |
| 2004/0088807 A1 | 5/2004 | Blaustein et al. |
| 2004/0091834 A1 | 5/2004 | Rizoiu et al. |
| 2004/0107521 A1 | 6/2004 | Chan et al. |
| 2004/0123409 A1 | 7/2004 | Dickie |
| 2004/0128778 A1 | 7/2004 | Wong |
| 2004/0129296 A1 | 7/2004 | Treacy et al. |
| 2004/0134001 A1 | 7/2004 | Chan |
| 2004/0143917 A1 | 7/2004 | Ek |
| 2004/0154112 A1 | 8/2004 | Braun et al. |
| 2004/0163191 A1 | 8/2004 | Cuffaro et al. |
| 2004/0168269 A1 | 9/2004 | Kunita et al. |
| 2004/0168272 A1 | 9/2004 | Prineppi |
| 2004/0177458 A1 | 9/2004 | Chan et al. |
| 2004/0187889 A1 | 9/2004 | Kemp et al. |
| 2004/0200016 A1 | 10/2004 | Chan et al. |
| 2005/0008986 A1 | 1/2005 | Sokol et al. |
| 2005/0189000 A1 | 9/2005 | Cacka et al. |
| 2005/0255427 A1 | 11/2005 | Shortt et al. |
| 2005/0266376 A1 | 12/2005 | Sokol et al. |
| 2008/0213731 A1 | 9/2008 | Fishburne |
| 2010/0055634 A1 | 3/2010 | Spaulding et al. |
| 2011/0041268 A1 | 2/2011 | Iwahori et al. |

FOREIGN PATENT DOCUMENTS

| | | |
|---|---|---|
| CN | 201223467 | 4/2009 |
| DE | 243224 | 4/1910 |
| DE | 1766651 | 12/1981 |
| DE | 3431481 | 2/1986 |
| DE | 3512190 | 10/1986 |
| DE | 8626725 | 5/1987 |
| DE | 3736308 | 7/1989 |
| DE | 4142404 | 7/1991 |
| DE | 4003305 | 8/1991 |
| DE | 4223195 | 1/1994 |
| DE | 4223196 | 1/1994 |
| DE | 4226658 | 2/1994 |
| DE | 4226659 | 2/1994 |
| DE | 4241576 | 6/1994 |
| DE | 4309078 | 9/1994 |
| DE | 29715234 | 12/1997 |
| DE | 29919053 | 12/2000 |
| DE | 19961447 | 7/2001 |
| EP | 0210094 | 6/1986 |
| EP | 0354352 | 2/1990 |
| EP | 0661025 | 7/1995 |
| EP | 0704180 | 4/1996 |
| FR | 429447 | 9/1911 |
| FR | 1171337 | 1/1959 |
| GB | 477799 | 1/1938 |
| GB | 500517 | 2/1939 |
| GB | 899618 | 6/1962 |
| GB | 1583558 | 8/1977 |
| GB | 2175494 | 12/1986 |
| GB | 2250428 | 6/1992 |
| JP | 53029847 | 3/1978 |
| JP | 53033753 | 3/1978 |
| JP | 3222905 | 10/1991 |
| SE | 324221 | 5/1970 |
| WO | WO 91/13570 | 9/1991 |

(56) References Cited

FOREIGN PATENT DOCUMENTS

| | | |
|---|---|---|
| WO | WO 91/19437 | 12/1991 |
| WO | WO 92/10146 | 6/1992 |
| WO | WO 92/16160 | 10/1992 |
| WO | WO 93/10721 | 6/1993 |
| WO | WO 93/15628 | 8/1993 |
| WO | WO 94/04093 | 3/1994 |
| WO | WO 94/26144 | 11/1994 |
| WO | WO 95/02375 | 1/1995 |
| WO | WO 95/33419 | 12/1995 |
| WO | WO 98/47443 | 10/1998 |
| WO | WO 01/28452 | 4/2001 |
| WO | WO 01/45582 | 6/2001 |
| WO | WO 02/071970 | 9/2002 |
| WO | WO 02/071971 | 9/2002 |
| WO | WO2005/063143 | 7/2005 |

OTHER PUBLICATIONS

Teledyne Water Pik "Plaque Control 3000" plaque removal instrument (Jul. 1991).

American Dentronics Incorporated "Soniplak" sonic plaque removal system (May 1993).

Teledyne Water Pik "Sensonic" Toothbrush, sales brochure (at least as early as Sep. 1994).

International Search Report and Written Opinion, PCT Application No. PCT/US2012/036092, 8 pages, Jul. 10, 2012.

* cited by examiner

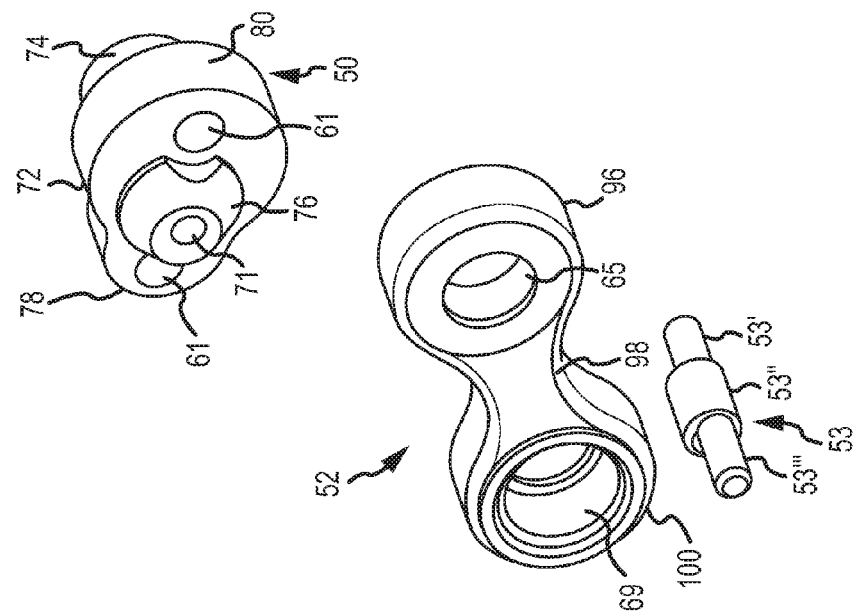
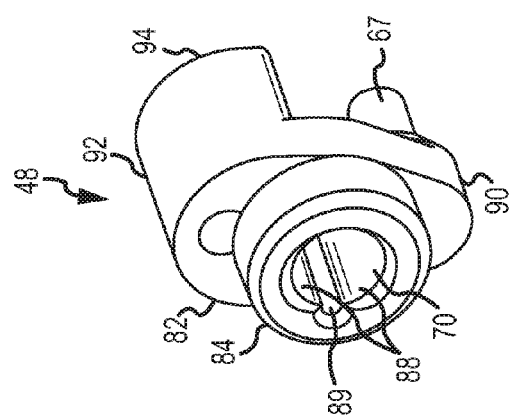
FIG. 11

MECHANICALLY-DRIVEN, SONIC TOOTHBRUSH SYSTEM

CROSS REFERENCE TO RELATED APPLICATIONS

The present application is a continuation of U.S. patent application Ser. No. 13/462,614, filed May 2, 2012, which claims priority pursuant to 35 U.S.C. §119(e) to U.S. provisional application No. 61/481,357 filed 2 May 2011 entitled "Mechanically driven sonic toothbrush system," which is hereby incorporated herein by reference in its entirety.

TECHNICAL FIELD

The present disclosure relates to oral health products. More specifically, the present invention relates to sonic toothbrush systems.

BACKGROUND

The state of the art in sonic toothbrush technology centers around drive systems that create a desired oscillating toothbrush output motion by using electro-magnetic drivers and centering return springs to directly create oscillating motion. No continuous input rotation or drivers are involved in these electro-magnetic systems and such electro-magnetic systems have a relatively high production cost.

There are also currently many toothbrushes that provide oscillating output brush motion from continuously rotating input drivers. Such mechanically-driven toothbrushes typically have a reduced manufacturing cost as compared to toothbrushes employing electro-magnetic drivers. However, such rotating systems all perform the oscillating function at speeds well below sonic level. There are no continuously rotating input drive systems that operate at sonic speeds.

The information included in this Background section of the specification, including any references cited herein and any description or discussion thereof, is included for technical reference purposes only and is not to be regarded subject matter by which the scope of the invention as defined in the claims is to be bound.

SUMMARY

One exemplary implementation of a mechanically-driven, sonic toothbrush includes an electric motor, a brush shaft, and a drive assembly. The electric motor may be a continuously rotating input driver (e.g., a DC motor) that drives a specifically balanced drive assembly with a linkage system to change the continuous rotation of the input driver into the desired oscillating output motion which drives the attached toothbrush head at a sonic speed(s). The electric motor includes a drive shaft. When the electric motor is actuated, the drive shaft continuously rotates until the motor is arrested. The drive assembly is coupled between the drive shaft and a brush shaft. The drive assembly is configured to convert the rotation of the drive shaft into sonic oscillation of a toothbrush supported on an end of the brush shaft.

In another implementation of the sonic toothbrush system, the drive assembly includes a coupler and an eccentric pin. The coupler has a first end and a second end. The first end is operably coupled to the brush shaft and the eccentric pin is rotationally received within the second end. The rotation of the drive shaft causes the eccentric pin to rotate within the second end. The rotation of the eccentric pin causes the coupler to oscillate.

In a further exemplary implementation, a sonic toothbrush may have an electric motor including a drive shaft, a brush shaft, and a drive assembly. When the electric motor is caused to operate, the drive shaft continuously rotates until the motor is caused to stop. The drive assembly may be coupled between the drive shaft and the brush shaft and configured to convert the rotation of the drive shaft into sonic oscillation of a toothbrush head supported on an end of the brush shaft.

In an additional exemplary implementation, a sonic toothbrush may provide oscillating bristle motion. The sonic toothbrush may include a continuously rotating drive system, a brush shaft, and a linkage between the drive system and the brush shaft that provides oscillating, sonic speed output motion to the brush shaft with an extremely low level of mechanical vibration and noise.

In yet another exemplary implementation, a method of designing a sonic toothbrush is disclosed. The sonic toothbrush may have a continuously rotating drive system, a brush shaft, and a linkage between the drive system and the brush shaft. The method may involve performing a finite element analysis on the linkage and then determining a weight distribution in the linkage based upon the finite element analysis to position a center of mass of the linkage and impart a balance or a selected imbalance to the linkage. The method may further involve adjusting one or more replaceable weights within the linkage to alter the center of mass or alter the selected imbalance.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. A more extensive presentation of features, details, utilities, and advantages of the present invention as defined in the claims is provided in the following written description of various embodiments of the invention and illustrated in the accompanying drawings.

BRIEF DESCRIPTION OF THE DRAWINGS

FIG. 11 is an exploded, front isometric view of the main components of the drive assembly of the mechanically-driven, sonic toothbrush system of FIG. 1.

DETAILED DESCRIPTION

Several exemplary embodiments of a mechanically-driven, sonic toothbrush system are disclosed herein. The sonic toothbrush system makes use of a continuously rotating input driver (e.g., a DC or AC motor) that operates a balanced linkage system to change the continuous rotation of the input driver into a desired oscillating output motion, which drives the attached toothbrush head at a sonic speed or speeds.

The mechanically-driven, sonic toothbrush system may have a lower production cost than the current electro-magnetic sonic toothbrush systems due to the use of DC drive motors for input drive motion and the use of relatively inexpensive molded plastic components. The mechanically-driven, sonic toothbrush system, due in part to its balance weights, allows its mechanical drive to provide sonic output motion with a low level of vibration and noise. The weights (i.e., plugs or other components of a selected mass) can be tailored to produce these reduced vibration and noise levels at various output oscillation speeds, from sub-sonic through sonic. This tailored weight aspect of the mechanical drive allows a single basic system design to be used for a wide range of sub-sonic through sonic brush outputs and models by changing the balance components during brush manufacture.

Thus, the exemplary mechanically-driven, sonic toothbrush systems disclosed herein may provide a continuously rotating input drive system that provides oscillating, sonic-speed toothbrush output motion with an extremely low level of mechanical vibration and noise. Also, the exemplary mechanically-driven, sonic toothbrush systems disclosed herein provide a sonic toothbrush system at a reduced production cost.

The use of "sonic" or "sonic speed" herein refers to the frequency of oscillation of the brush head of the toothbrush and means that such frequency is within the range of sound frequencies (i.e., between 20 Hz and 20,000 Hz). Typically, sonic toothbrushes operate at a range of between 200 and 300 cycles per second. In exemplary implementations of the disclosed mechanically-driven, sonic toothbrush system disclosed herein, the motor may operate at between 200 and 300 rotations per second (i.e., between 12,000 and 18,000 rpm).

Figure 1:
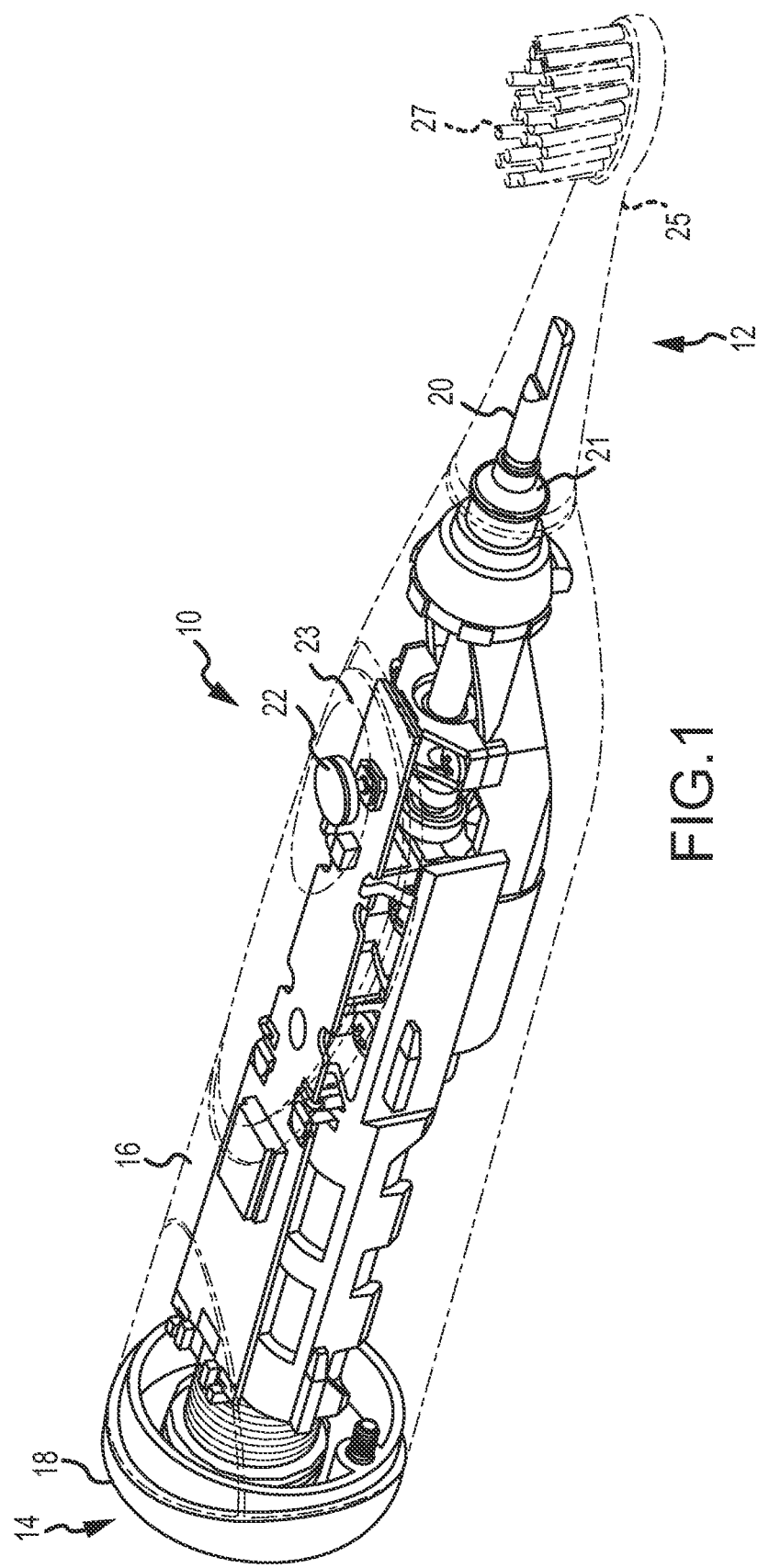
FIG. 1 is a brush end isometric view of an exemplary implementation of a mechanically-driven, sonic toothbrush system.

An exemplary embodiment of a mechanically-driven, sonic toothbrush system 10 disclosed herein is depicted in FIG. 1, which is a brush end isometric view of the system 10. As shown in FIG. 1, the system 10 includes a brush end 12, a base end 14 opposite the brush end, a housing 16 extending between the ends 12, 14 and forming the surface of the system 10, and a generally flat base 18 on which the system 10 may be stood upright on a planar surface, such as a countertop. A brush shaft 20 extends out of the housing 16 at the brush end 12 from the system drive assembly enclosed by the housing 16 and discussed below. A shaft seal 21 extends about the shaft 20 between the housing 16 and shaft 20 at the brush end 12 and is configured to allow the shaft 20 to oscillate while preventing the ingress of fluids into the interior of the housing.

The housing 16 may be generally cylindrically shaped to ergonomically fit in the hand of a user. The cylindrical shape may taper in the direction of the brush end 12 approximately one third the length of the housing 16 from the brush end 12. A control button 22 is supported on the housing 16 and actuates the system drive assembly between on and off and additionally, in some instances, between a range of speeds. A face plate 23 is supported on the housing 16 in a region extending about the control button 22. A toothbrush 25 (shown in phantom lines) is mounted on the end of the brush shaft 20. The toothbrush 25 includes a plurality of bristles 27.

Figure 2:
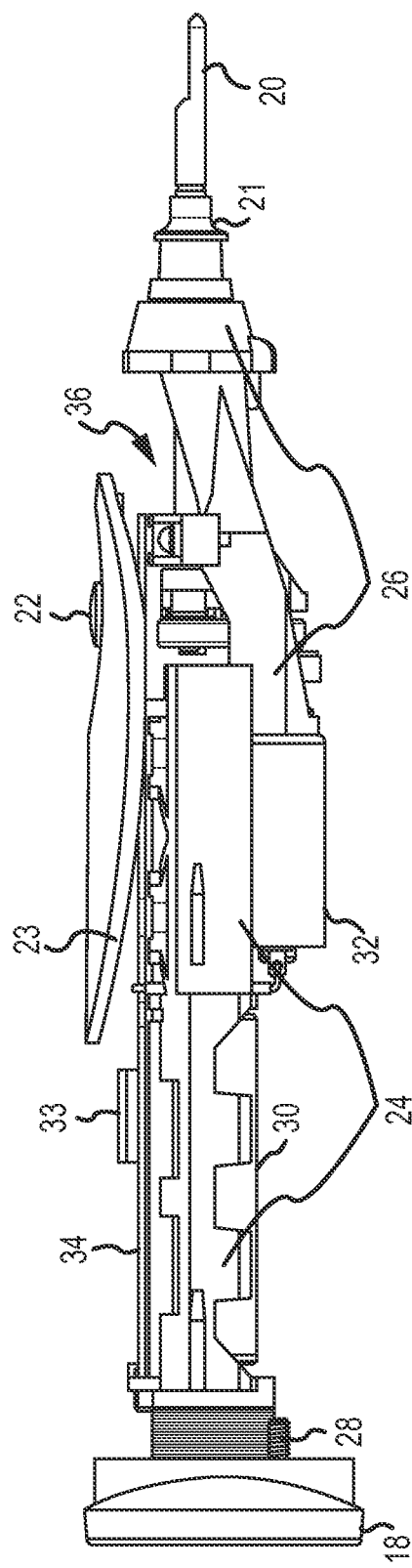
FIG. 2 is a side view of the mechanically-driven, sonic toothbrush system of FIG. 1 with the housing removed.
Figure 3:
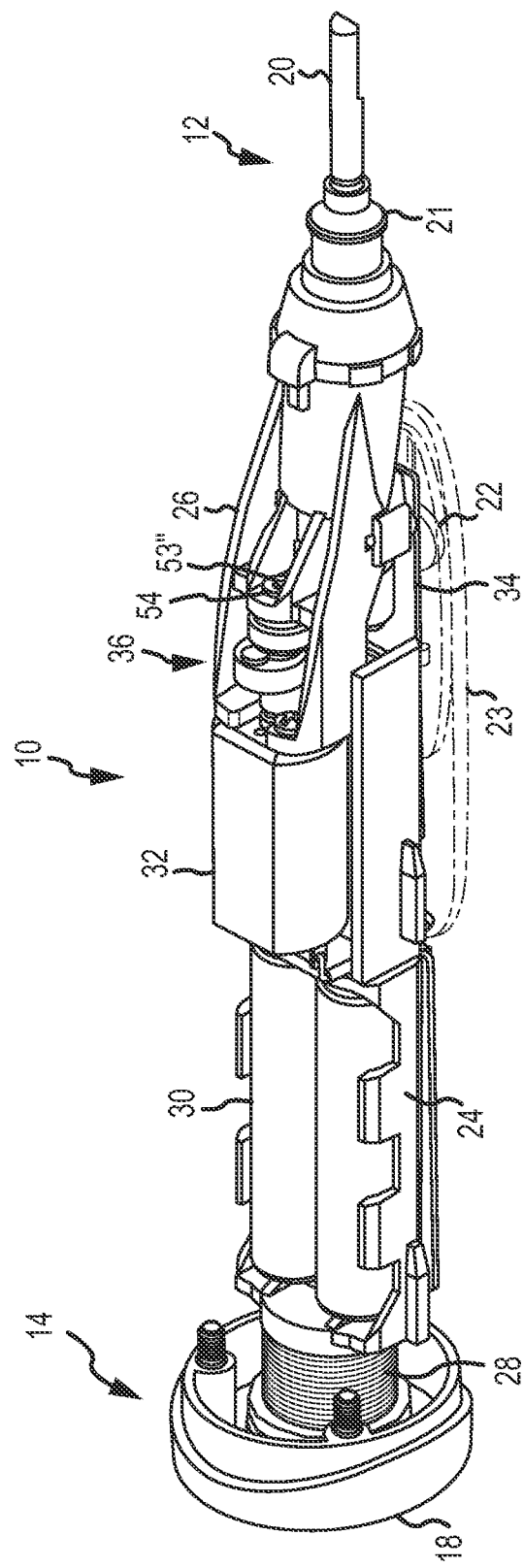
FIG. 3 is a bottom isometric view of the mechanically-driven, sonic toothbrush system of FIG. 1 with the housing removed.

As shown in FIGS. 2 and 3, which are, respectively, a side view and a bottom isometric view of the system 10 with the housing 16 removed, the system 10 includes an internal support structure formed by a chassis 24 extending towards the base end 14 and a drive bracket or chassis 26 extending towards the brush end 12. An induction coil 28 is wound around a bobbin and is located between the interior side of the flat base 18 and a base end 14 side of the chassis 24. A rechargeable battery pack 30 is electrically coupled to the induction coil 28 and supported in a pocket of the chassis 24 on a brush end 12 side of the charger coil 28.

As illustrated in FIGS. 2 and 3, an electric DC motor 32 is supported off of the chassis 24 and drive bracket 26 near the overlap of these structures. The motor 32 is electrically coupled to the battery pack 30 via electrical control circuits 33 of a printed circuit board 34 supported off of the chassis 24 and drive bracket 26. The electrical control circuits 33 are actuated via the control button 22 to cause the motor 32 to operate at different states (e.g., on, off, high speed, low speed, etc.). In one embodiment, the electrical control circuits 33 controlling the motor 32 include one or more trim pots that allow precise control of frequency and motor speed.

Figure 4:
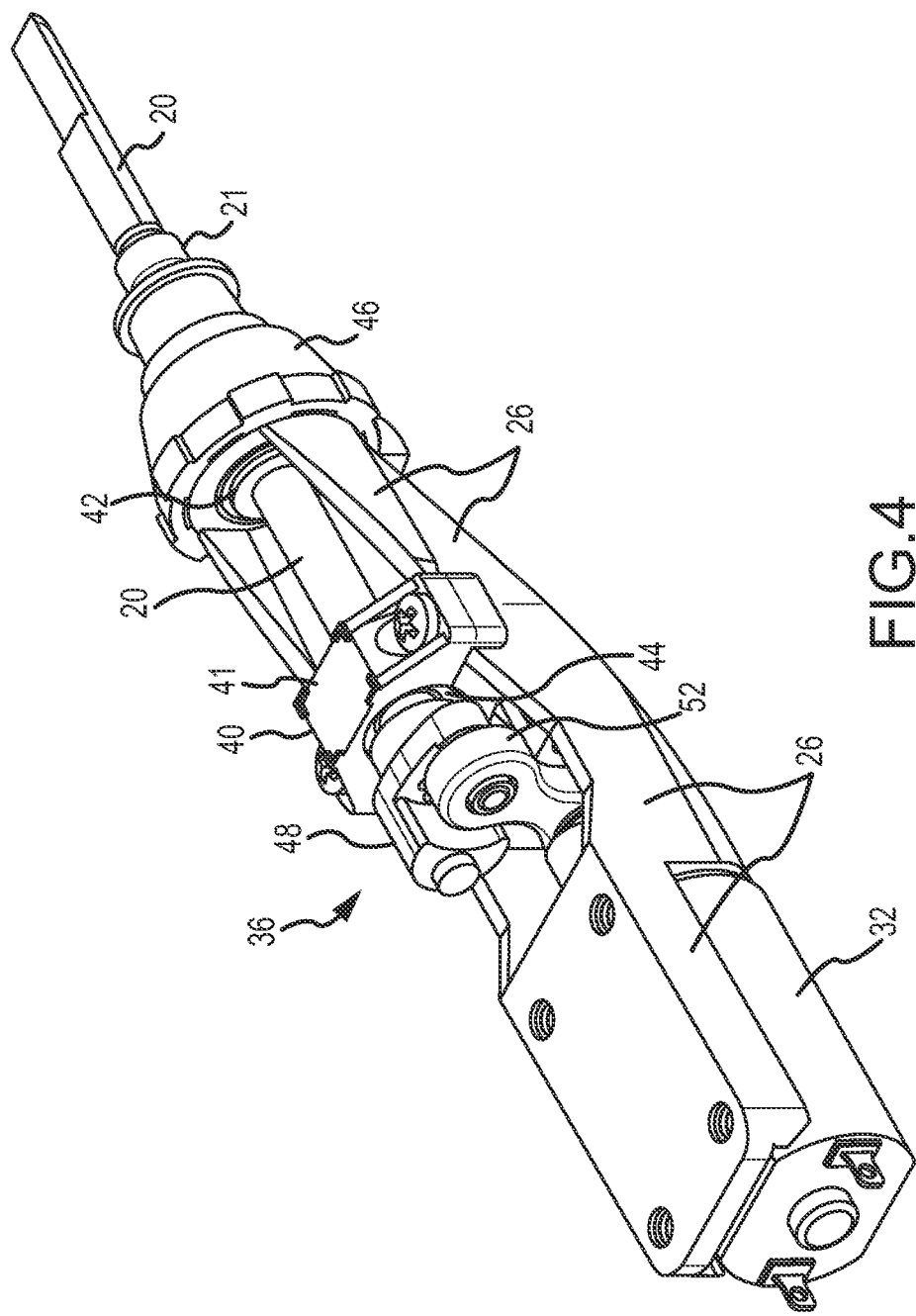
FIG. 4 is a top isometric view of the drive bracket of the mechanically-driven, sonic toothbrush system of FIG. 1 and the components supported thereon.
Figure 5:
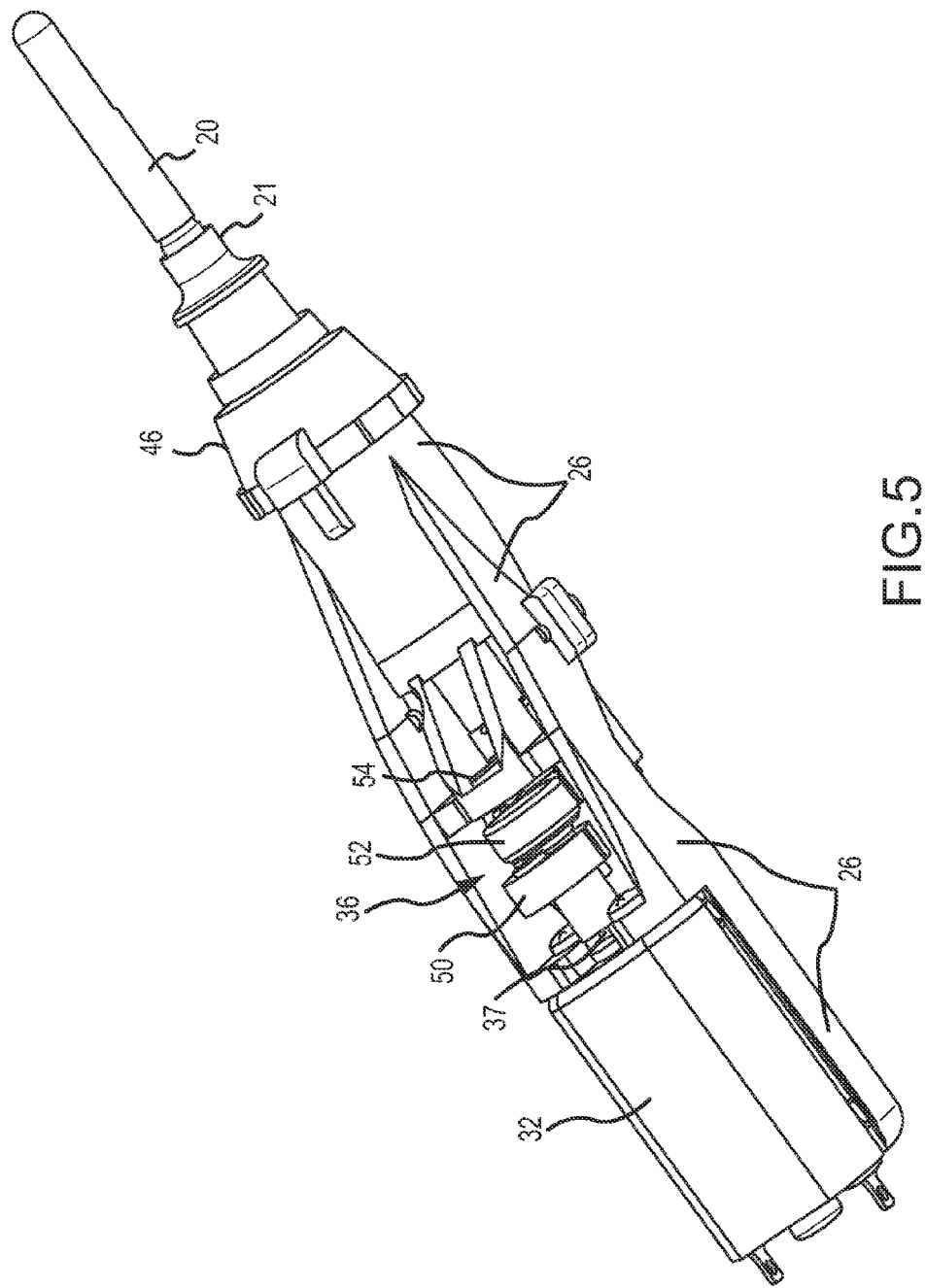
FIG. 5 is a bottom isometric view of the drive bracket of the mechanically-driven, sonic toothbrush system of FIG. 1 and the components supported thereon.

As depicted in FIGS. 4 and 5, which are, respectively, a top isometric view and a bottom isometric view of the drive bracket 26 and the components supported thereon, the system drive assembly 36 is supported within a pocket of the drive bracket 26. The drive assembly 36 mechanically couples the output shaft 37 of the motor 32 to the brush shaft 20 to cause the brush shaft 20 to oscillate at sonic speeds when the motor 32 causes its output shaft 37 to continuously rotate.

Figure 6:
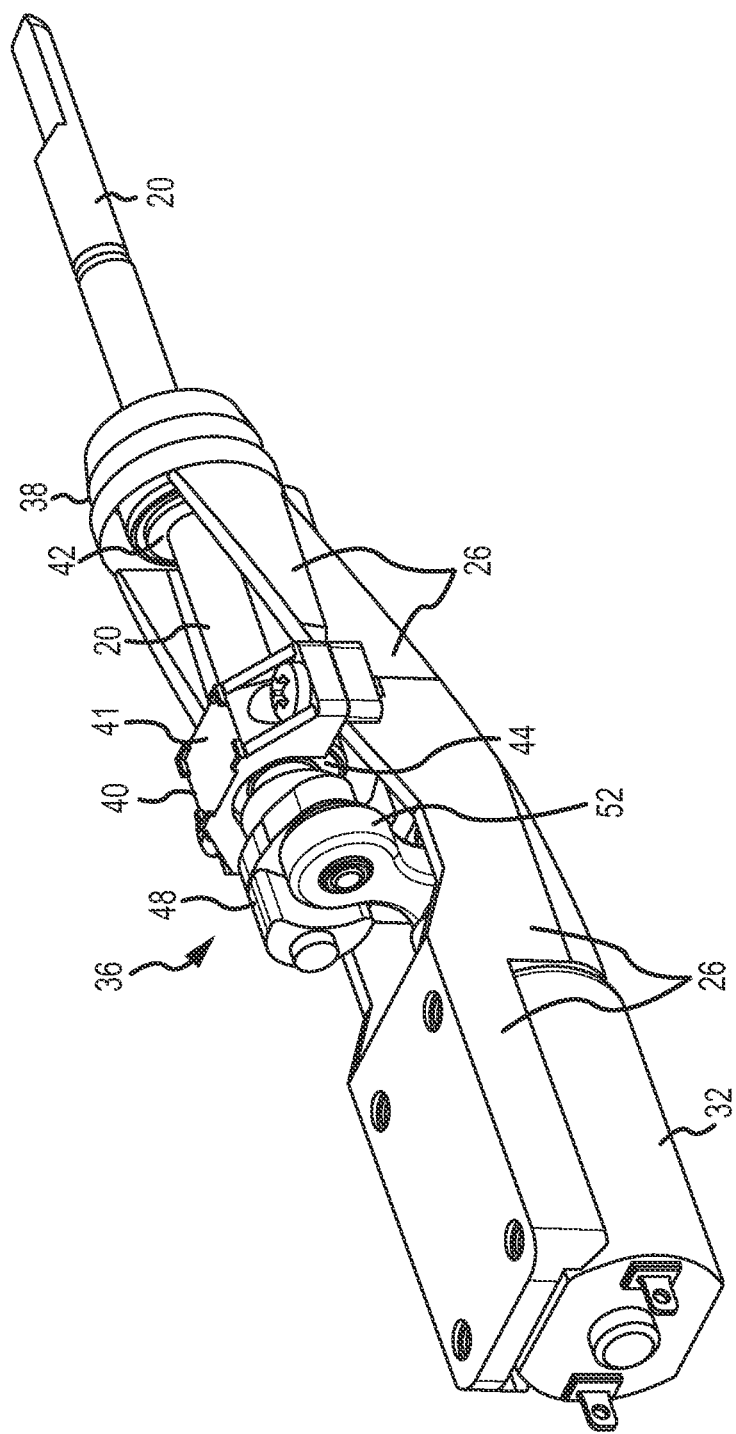
FIG. 6 is a top isometric view of the mechanically-driven, sonic toothbrush system of FIG. 1 drive bracket and the components supported thereon.
Figure 7:
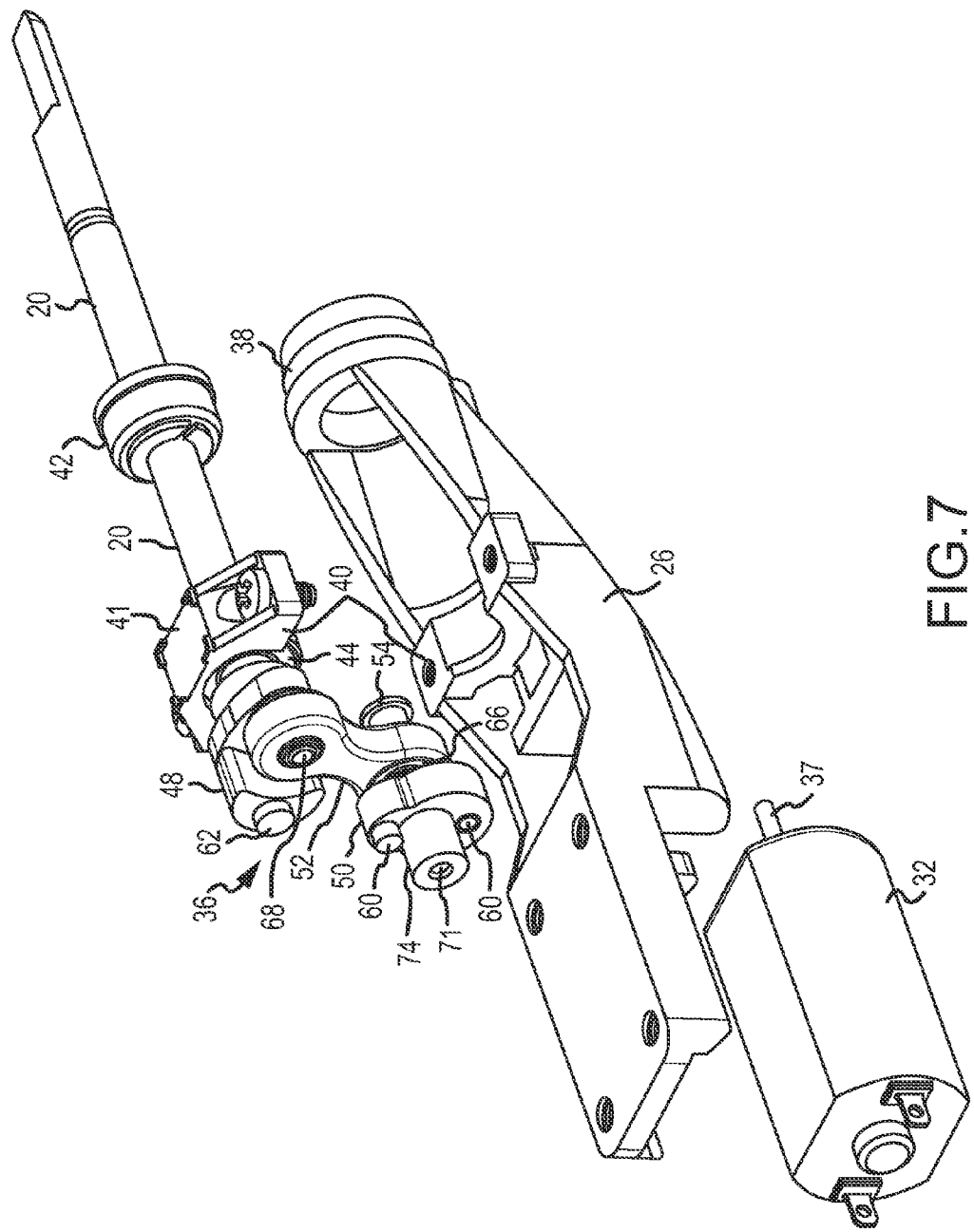
FIG. 7 is a partially exploded view of the drive bracket of the mechanically-driven, sonic toothbrush system of FIG. 1 and the components supported thereon.
Figure 10:
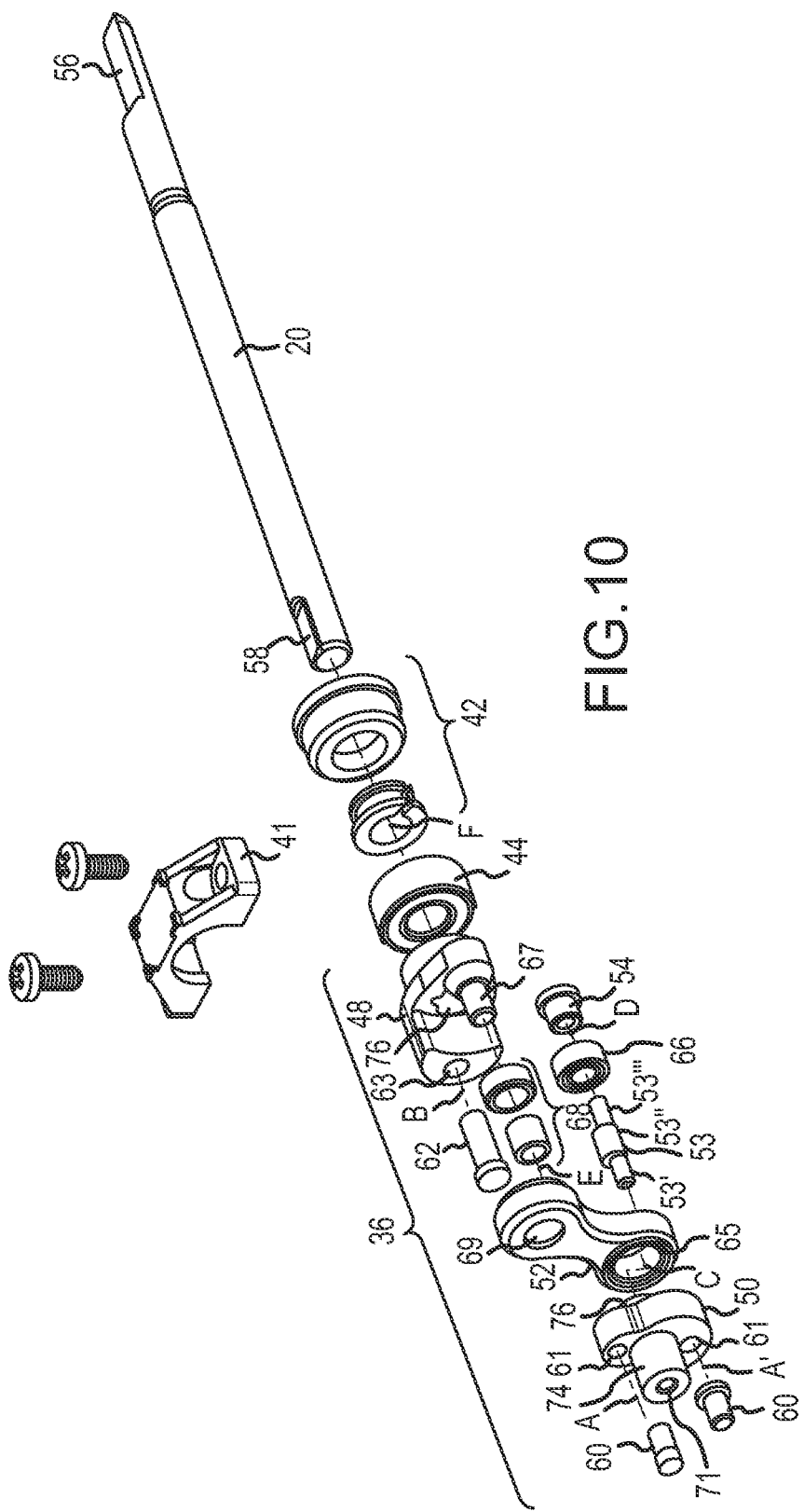
FIG. 10 is an exploded isometric view of the drive assembly and brush shaft of the mechanically-driven, sonic toothbrush system of FIG. 1.

As illustrated in FIGS. 6, 7 and 10, which are, respectively, a top isometric view and first and second partially exploded views of the drive bracket 26 and the components supported thereon, the drive bracket 26 includes a front bearing ring 38 and a rear bearing ring 40. The rear bearing ring 40 may be multi-piece with a bearing bracket 41 forming the upper portion of the bearing ring 40 mounted to the drive bracket 26, which forms the lower portion of the rear bearing ring 40. The front bearing ring 38 includes a bushing or bearing 42, and the rear bearing ring 40 includes a bushing or bearing 44. The bearings 42, 44 may be ball or roller type bearings in some embodiments. The bearing 44 of the rear bearing ring 40 supports the rear end of the brush shaft 20, and the bearing ring 42 of the front bearing ring 38 supports the brush shaft 20 near the midpoint of the brush shaft 20.

As can be understood from a comparison of FIGS. 4 and 5 to FIG. 6, an isolator damper 46 extends about the front bearing ring 38 and acts to vibrationally isolate the moving components of the system 10 from the housing 16 that surrounds the damper 46 and moving components of the system 10.

Figure 8:
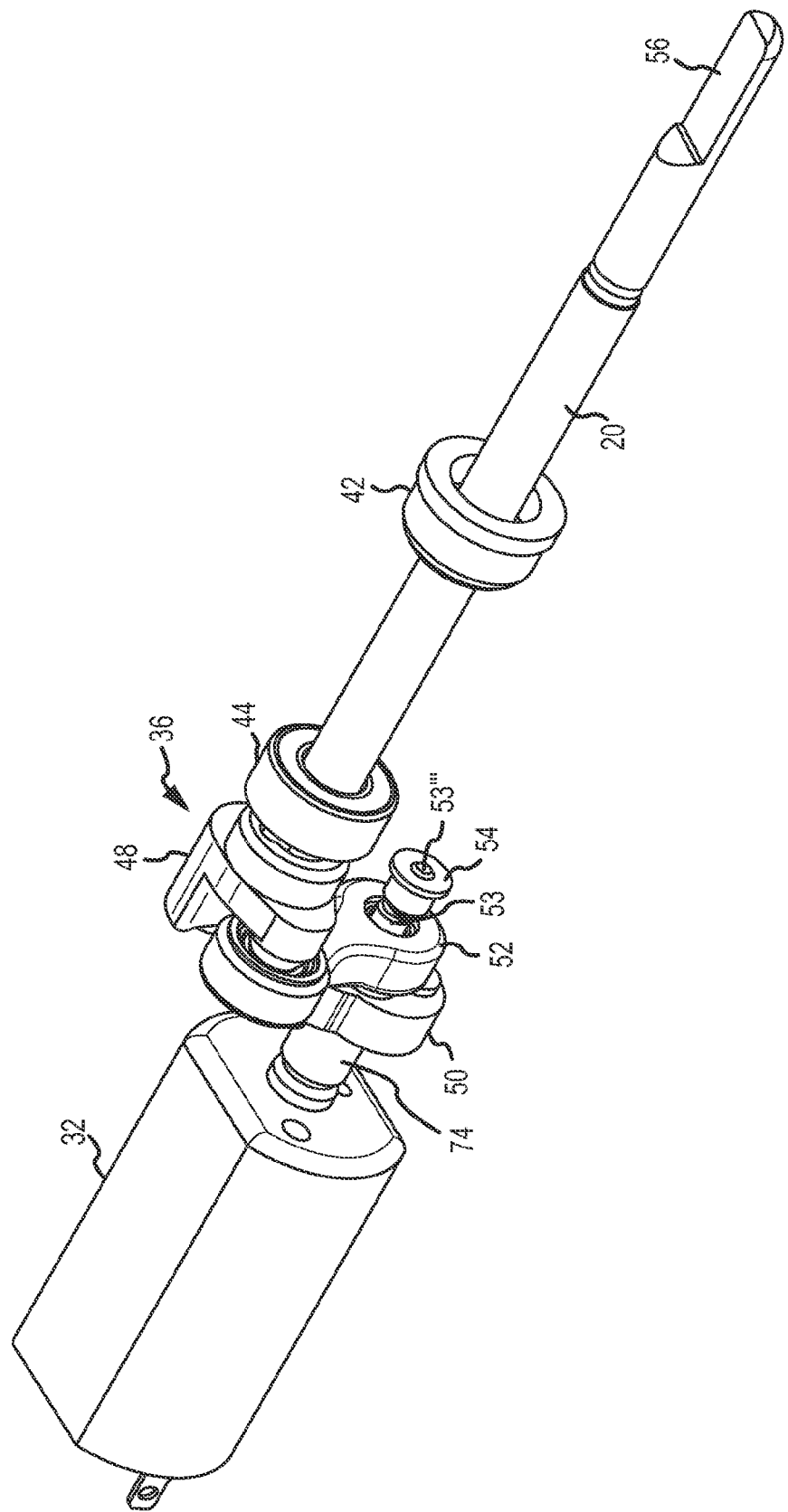
FIG. 8 is a front isometric view of the brush shaft, drive assembly, and motor of the mechanically-driven, sonic toothbrush system of FIG. 1 mechanically coupled together for operation.

As shown in FIG. 8, which is a front isometric view of the brush shaft 20, the drive assembly 36 and the motor 32 are mechanically coupled together for operation. The bearings 42, 44 support the shaft 20 and the rear end of the shaft 20 is received in a rocker arm 48 forming a front end of the drive assembly 36. Also, the motor output shaft 37 extends into a motor crank arm 50 forming a rear end of the drive assembly 36. The motor crank arm 50 is coupled to the rocker arm 48 via a dog bone coupler 52. An eccentric pin 53 extends from the motor crank arm 50 and through a lower portion of the coupler 52 to be received in a support bushing 54. The eccentric pin 53 acts as a cam and causes the lower portion of the coupler 52 to revolve about the axis of the motor shaft 37.

Figure 9:
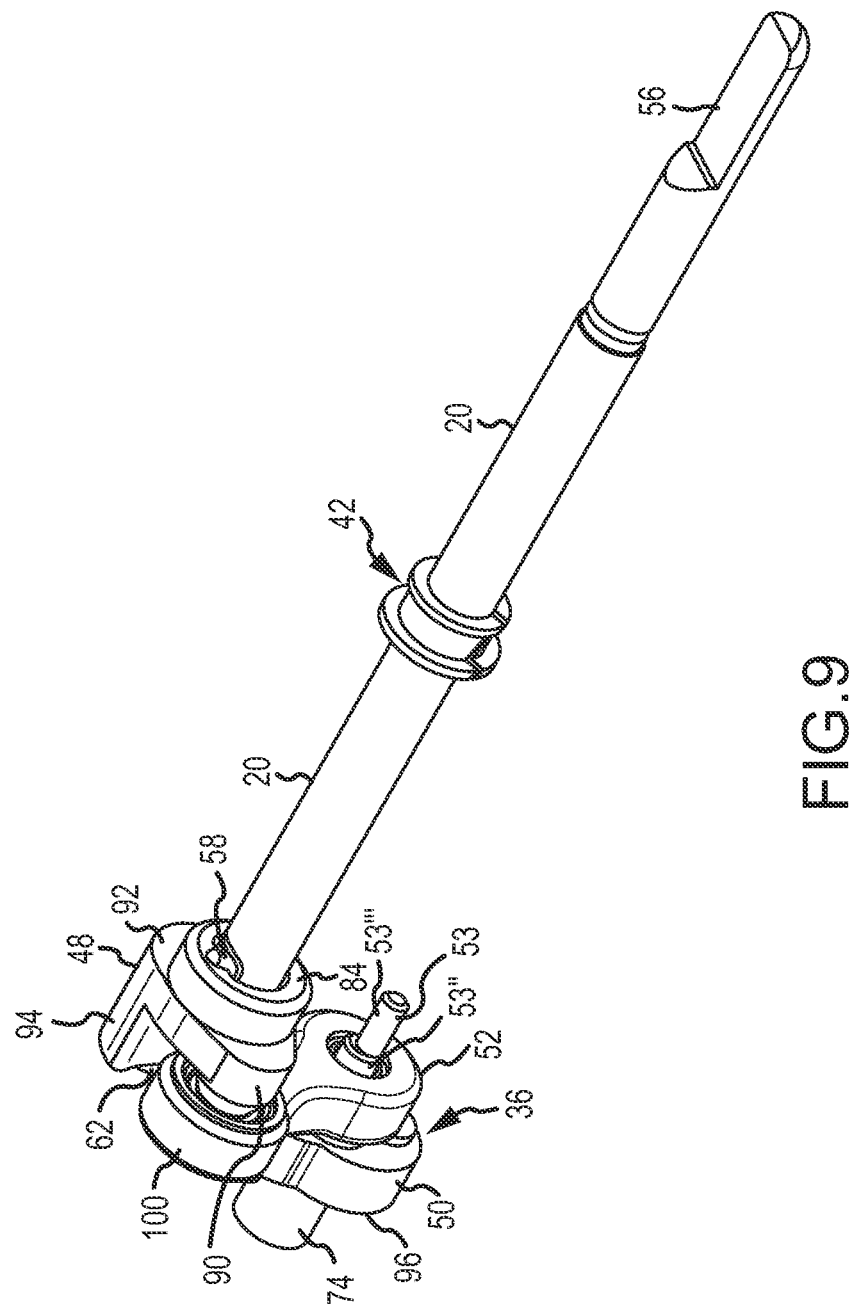
FIG. 9 is the same view as FIG. 8 with the motor, rear bearing, and bushing removed.

As indicated in FIG. 9, which is the same view as FIG. 8, with the motor 32, the rear bearing 44, and the bushing 54 removed, the front end of the brush shaft 20 is configured to engage with a brush head (not shown). For example, the brush shaft 20 may include a flat region 56 at its front end. The rear end of the brush shaft 20 is configured to engage 48 with the rocker arm 48. For example, the brush shaft 20 may include a flat region 58 at its rear end.

As shown in FIG. 10, which is an exploded isometric view of the drive assembly 36 and the shaft 10, the motor crank arm 50 includes balance weights 60 that are fixedly received in apertures 61 in the motor crank arm 50, as indicated by dashed lines identified at A and A'. Similarly, the rocker arm 48 includes a balance weight 62 that is fixedly received in an aperture 63 in the rocker arm 48, as indicated by the dashed line identified at B. The weights 60, 62 may act to counterbalance the components of the drive assembly 36 on which the weights 60, 62 are mounted to reduce noise and vibration in the drive assembly 36.

As illustrated in FIG. 10, a rearward end 53' of the eccentric pin 53 is fixedly received in the motor crank arm 50, as indicated by the dashed line identified at C. An enlarged diameter eccentric mid portion 53" of the eccentric pin 53 is rotationally received in a bearing 66, which is fixedly received in a lower aperture 65 of the dog bone coupler 52, and the forward end 53'" of the eccentric pin 53 is rotationally received in the bushing 54. All of this indicated by the dashed line identified at D. The pivot pin 67 of the rocker arm 48 is pivotally or oscillatingly received in a bearing 68, which is fixedly received in an upper aperture 69 of the dog bone coupler 52, as indicated by the dashed line identified at E. Finally, as explained above, the brush shaft 20 is pivotally or oscillatingly located within the bearings 42, 44, and the rearward end of the shaft 20 is fixedly received in an aperture 70 the rocker arm 48, all of this indicated by the dashed line identified at F.

Figure 12:
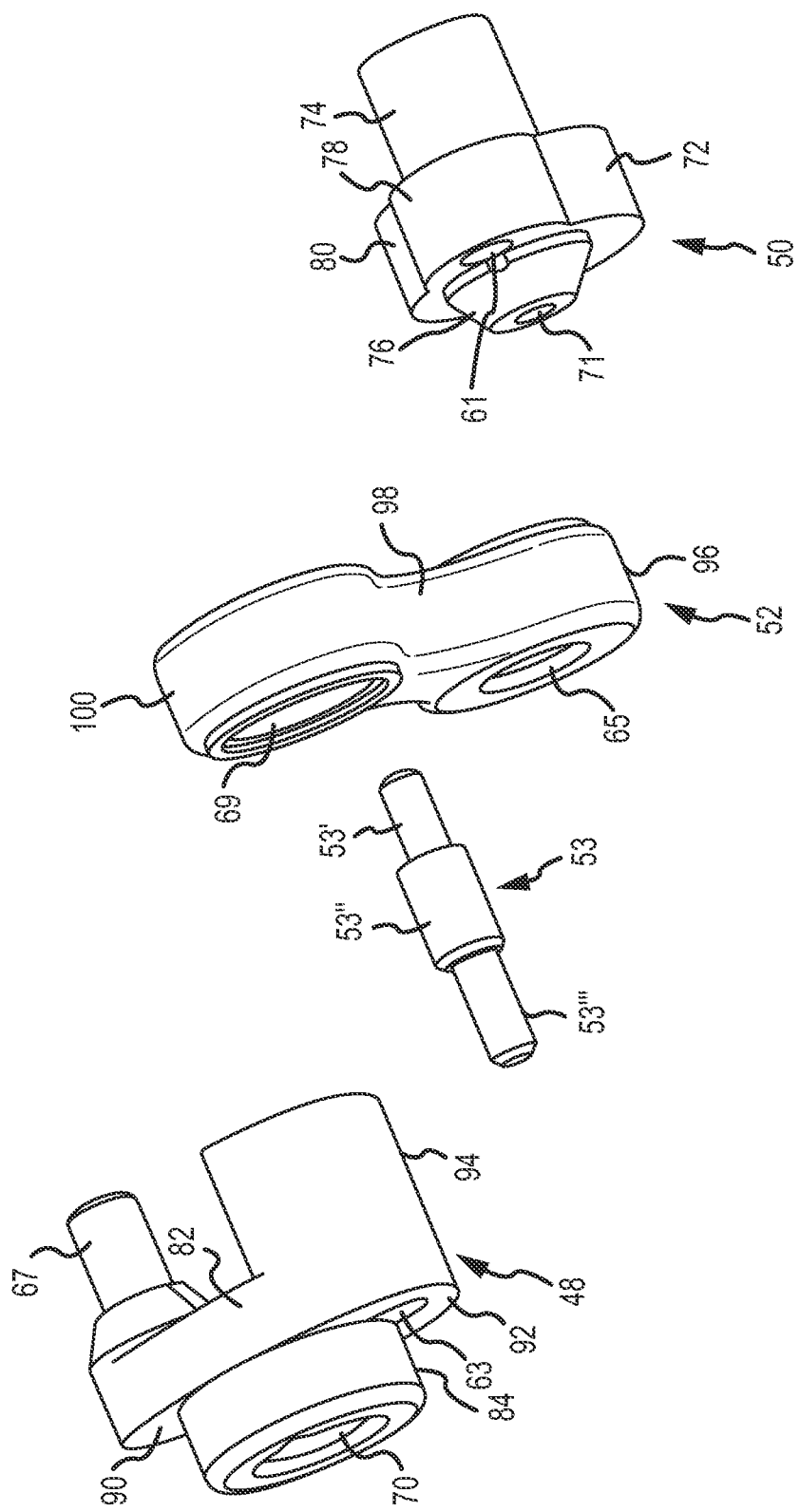
FIG. 12 is an exploded, side isometric view of the main components of the drive assembly of the mechanically-driven, sonic toothbrush system of FIG. 1.
Figure 13:
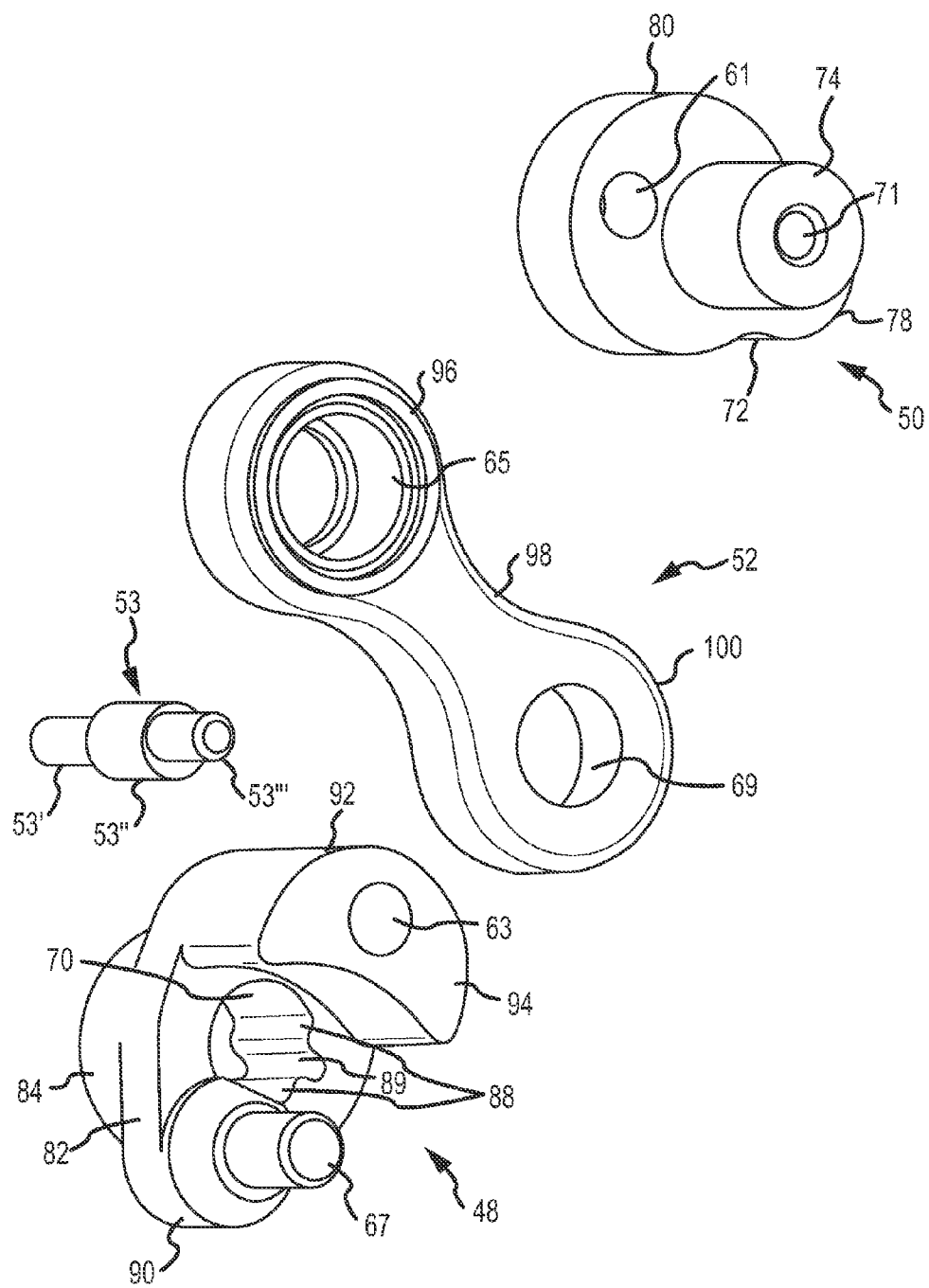
FIG. 13 is an exploded rear isometric view of the main components of the drive assembly of the mechanically-driven, sonic toothbrush system of FIG. 1.

For a discussion of the features of some of the main components of the drive assembly 36, reference is made to FIGS. 11, 12 and 13. FIG. 11 is an exploded, front isometric view of the main components of the drive assembly 36. FIG. 12 is an exploded, side isometric view of the main components of the drive assembly 36. FIG. 13 is an exploded, rear isometric view of the main components of the drive assembly 36. As illustrated in FIGS. 11, 12 and 13, the motor crank arm 50 includes a central axis aperture 71, a dual lobe portion 72, a cylindrical portion 74, a conical portion 76, and apertures 61 for receiving the balance weights 60. The lobe portion 72 has a small lobe 78 and a large lobe 80 opposite the central axis aperture 71 from the small lobe 78. The lobes 78, 80 each include a weight-receiving aperture 61, generally centered in the respective lobe 78, 80. The cylindrical portion 74 extends rearward of the lobe portion 72 and the conical portion 76 extends forward of the lobe portion 72. The central axis aperture 71 extends rearward to forward through the motor crank arm 50, starting at the most rearward face of the cylindrical portion 74 and ending at the most forward face of the conical portion 76. The central axis aperture 71 is generally coaxial with the axis of the cylindrical portion 74.

As depicted in FIGS. 11, 12 and 13, the rocker arm 48 includes a lobed portion 82, a cylindrical portion 84, and a central axis aperture 70. The cylindrical portion 84 extends forwardly from the lobed portion 82. The central axis aperture 70 is generally coaxial with the axis of the cylindrical portion 84 and is shaped to fixedly engage the rearward end of the brush shaft 20, for example, the central axis aperture 70 may have a flat region 88 to correspond to the flat region 58 of the brush shaft and may further have a slot or keyway 89 to provide an additional engagement feature). The lobed portion 82 includes a tapered lobe 90 and a rounded lobe 92 opposite the central axis aperture 61 from the tapered lobe 90. The tapered lobe 90 includes a pivot pin 67 extending rearward from the tapered lobe 90 and having an axis generally parallel to the axis of the central axis aperture 70. The rounded lobe 92 includes a weighted region 94 of increased thickness extending rearward from the rounded lobe 92 and having the aperture 63 for receiving the weight 62.

As indicated in FIGS. 11, 12 and 13, the eccentric pin 53 includes a rearward end shaft 53', an enlarged diameter eccentric mid portion 53", and a forward end shaft 53'". The rearward end shaft 53' extends rearward from the mid portion 53" and the forward end shaft 53'" extends forward from the mid portion 53". As can be understood from FIGS. 11, 12 and 13, the rearward end shaft 53' and the forward end shaft 53'" share a common pivot axis, while the enlarged eccentric mid portion 53" is eccentric relative to the forward and rearward end shafts 53', 53'" and has a pivot axis offset, but parallel to, the common pivot axis of the forward and rearward end shafts 53', 53'".

As shown in FIGS. 11, 12 and 13, the dog bone coupler 52 may have an hourglass shape and include a first rounded end portion 96 (motor crank arm engaging portion) extending into a reduced diameter mid portion 98 that extends into a second rounded end portion 100 (rocker arm engaging portion). The first end portion 96 includes an aperture 65 that receives the conical portion 76 of the motor crank arm 50 and the eccentric pin 53. The second end portion 100 includes an aperture 69 that receives the pivot pin 67 of the rocker arm 48. In one embodiment, the bearing 66 used in the dog bone coupler 52 is a model R 133ZZS and the bearing 44 utilized for the output brush shaft 20 is a model MR 104ZZ ball bearing.

Figure 14:
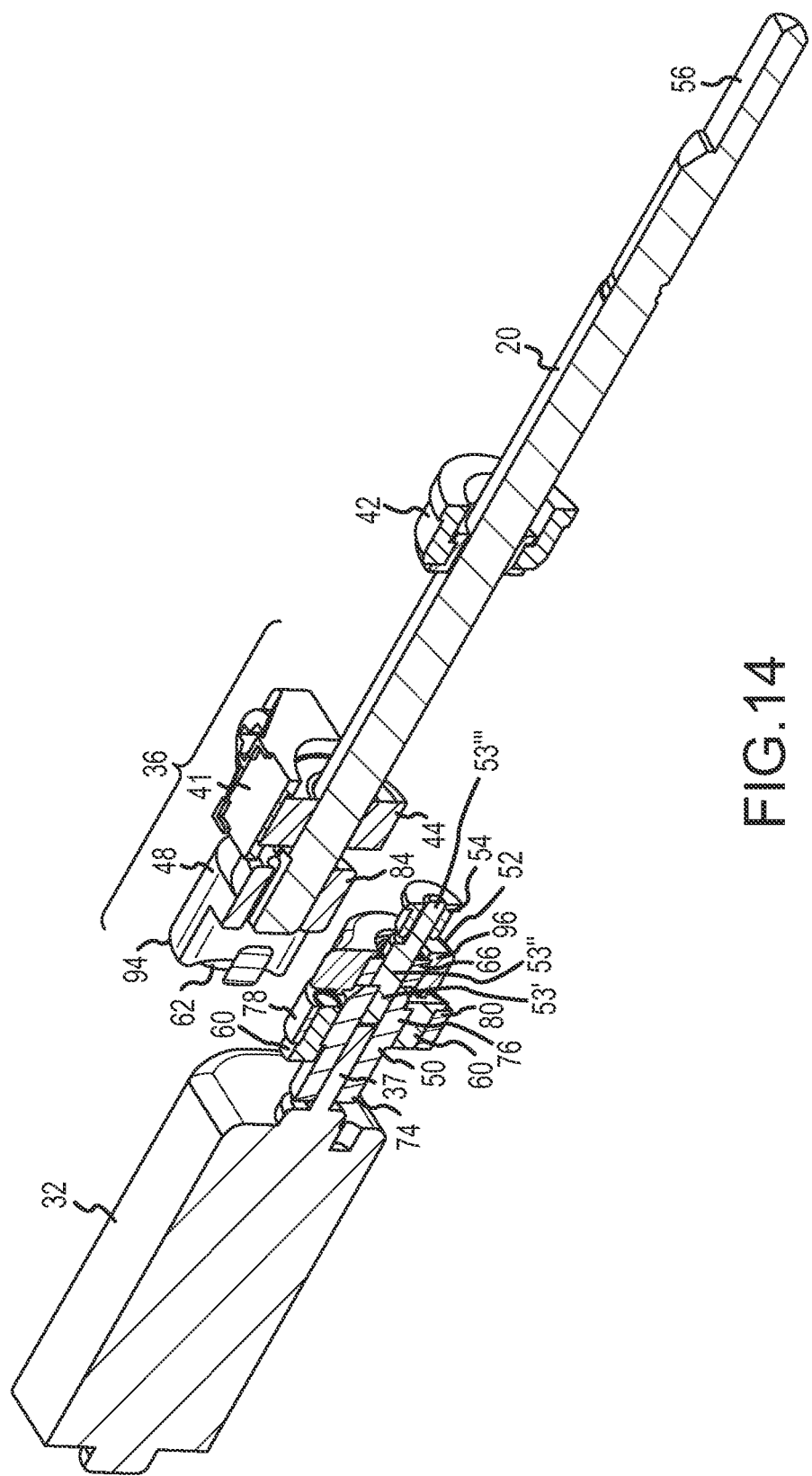
FIG. 14 is generally the same isometric view of the motor, drive assembly, and brush shaft as depicted in FIG. 8, further depicting a cross section extending through the axis of the motor drive shaft and the eccentric pin.
Figure 15:
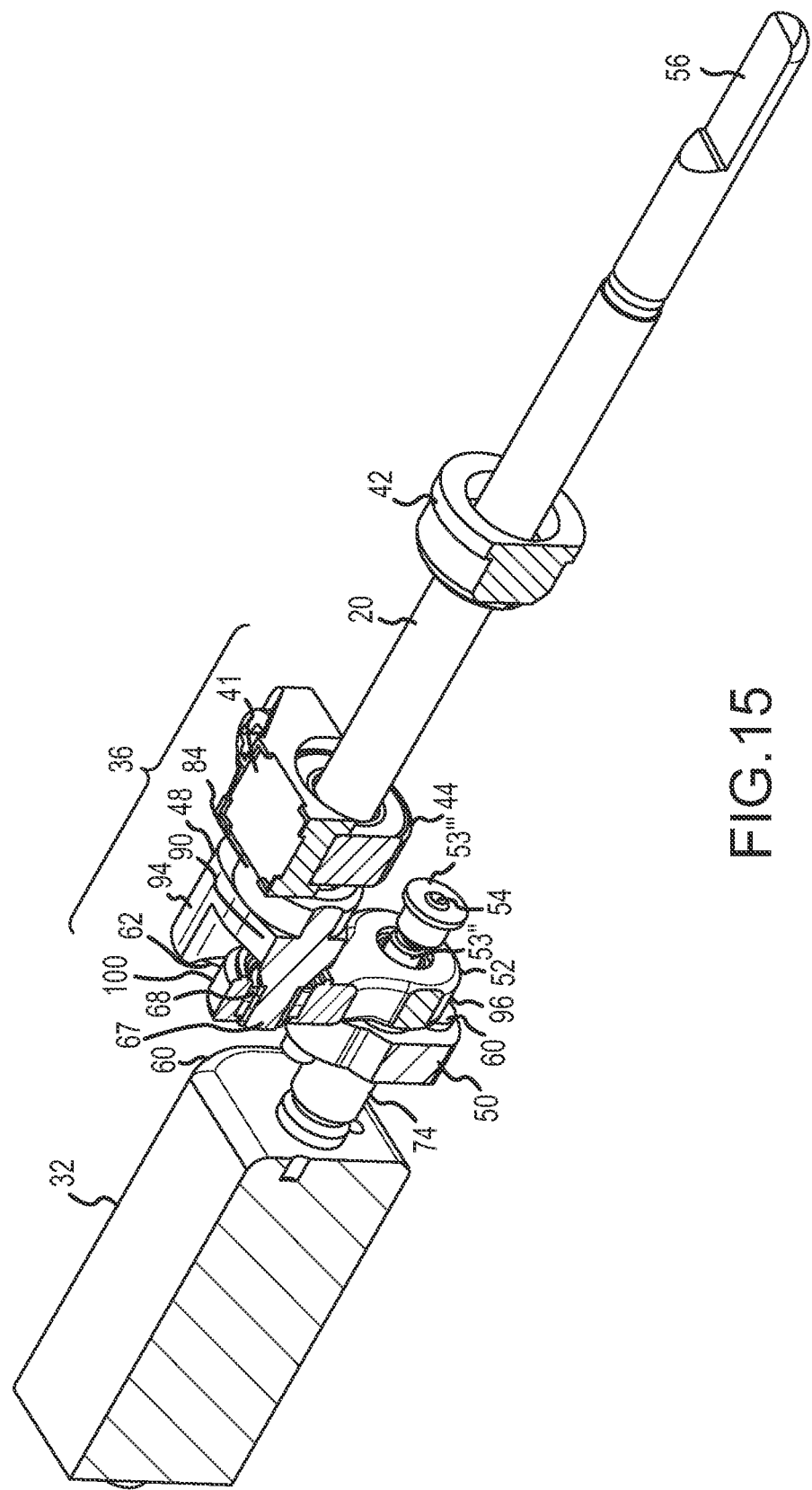
FIG. 15 is generally the same isometric view of the motor, drive assembly and brush shaft as depicted in FIG. 8, further depicting a cross section extending through the axis of the pivot pin of the rocker arm.

For a discussion of the operation of the drive assembly 36, wherein continuous rotation of the motor drive shaft 37 in a single rotational direction results in the drive assembly 36 causing the brush shaft 20 to oscillate back and forth, reference is made to FIGS. 8, 14 and 15. FIG. 14 is generally the same isometric view of the motor 32, drive assembly 36 and brush shaft 20 as depicted in FIG. 8, except a cross section is shown extending through the axis of the motor drive shaft 37 and the eccentric pin 53. FIG. 15 is generally the same isometric view of the motor 32, drive assembly 36, and brush shaft 20 as depicted in FIG. 8, except a cross section extending through the axis of the pivot pin 67 of the rocker arm 48 is shown.

As can be understood from FIGS. 8 and 14, once the motor 32 is actuated by the control button 22 to turn on and run, the motor drive shaft 37, which is fixedly received in the central axis aperture 71 (see FIGS. 11-13) of the motor crank arm 50, rotates continuously in a single rotational direction until the control button 22 is turned to off to stop the motor 32. The rearward end shaft 53' of the eccentric pin 53 is fixedly received in the central axis aperture 71 of the crank arm 50. The enlarged eccentric mid portion 53" of the eccentric pin 53 is rotationally received within the bearing 66, which is fixedly received in the aperture 65 (see FIGS. 11-13) of the dog bone coupler 52. The forward end shaft 53'" of the eccentric pin 53 is rotationally received in the bushing 54, which is mounted in a fixed position on the drive bracket 26 as shown in FIG. 3. Thus, the rotating motor drive shaft 37 causes the motor crank arm 50 and eccentric pin 53 to rotate in the same direction. Thus, the enlarged eccentric mid portion 53" and the forward end shaft 53'" of the eccentric pin 53 rotate in the same direction, respectively, within the bearings 66, 54. The rotation of the enlarged eccentric mid portion 53" causes the dog bone coupler 52 to move back and forth or, in other words, oscillate.

As can be understood from FIGS. 8, 14 and 15, the pivot pin 67 is pivotally or oscillatingly received in the bearing 68, which is fixedly received in the aperture 69 (see FIGS. 11-13) of the dog bone coupler 52. Thus, the back and forth or oscillating displacement of the dog bone coupler 52 causes the tapered lobe 90 to displace back and forth or oscillate about the axis of the central axis aperture 70 (see FIGS. 11-13) of the rocker arm 48. As a result, the rocker arm 48 and the brush shaft 20 are caused to pivot back and forth or oscillate about the longitudinal axis of the shaft 20.

As can be understood from the preceding discussion, in some embodiments, the drive assembly 36 used to convert the rotary motor motion into oscillating output brush shaft motion may be a four bar linkage. The required balance/imbalance of the various linkage components is related to the desired operational speed as well as the desired displacement of the oscillating output motion (i.e., different operational speeds and oscillating motion displacements employ different component balance/imbalance). In one embodiment, a design software program (e.g., finite element analysis software) may be used to calculate the desired center of mass locations of the various linkage components to minimize vibration and noise based on the desired design operational speed and displacement. The specific size and location of the balance/counterbalance weights 60, 62 for each component may then be finalized based on the mass of the material used for a component and the space constraints of the mechanism envelope in order to satisfy the desired resultant center of mass locations.

In exemplary embodiments, the motor drive shaft 50, dog bone coupler 52, rocker arm 48, and brush shaft 20 may be formed of a polymer material, while the weights 60, 62 may be formed of a metal material such as, for example, stainless steel, tungsten, etc. In other embodiments, the aforementioned drive assembly components and weights may be formed of other materials.

All directional references (e.g., proximal, distal, upper, lower, upward, downward, left, right, lateral, longitudinal, front, back, top, bottom, above, below, vertical, horizontal, radial, axial, clockwise, and counterclockwise) are only used for identification purposes to aid the reader's understanding of the present invention, and do not create limitations, particularly as to the position, orientation, or use of the invention. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. The exemplary drawings are for purposes of illustration only and the dimensions, positions, order and relative sizes reflected in the drawings attached hereto may vary.

The above specification, examples and data provide a complete description of the structure and use of exemplary embodiments of the invention as defined in the claims. Although various embodiments of the claimed invention have been described above with a certain degree of particularity, or with reference to one or more individual embodiments, those skilled in the art could make numerous alterations to the disclosed embodiments without departing from the spirit or scope of the claimed invention. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the invention as defined in the following claims.

What is claimed is:
1. A toothbrush comprising
   a handle;
   a brush head having a first end connected to the handle and a plurality of bristles positioned on a second end opposite the first end;
   a motor received within the handle;
   a brush shaft connected to the brush head and connected to the motor; and
   a linkage coupled between the motor and the brush shaft, the linkage comprising
      a coupler having a first end operably coupled to the brush shaft and a second end; and
      an eccentric pin connected to the motor and rotationally received at least partially within the second end of the coupler, the eccentric pin having a first axis axially aligned with an output axis of the motor and a second axis axially offset from the output axis of the motor.
2. The toothbrush of claim 1, wherein the coupler is connected to the brush shaft on a first side and connected to the eccentric pin on a second side opposite the first side.
3. The toothbrush of claim 1, further comprising a power source housed within the handle and electrically connected with the motor.
4. The toothbrush of claim 1, further comprising a bracket to which the motor is attached and to which the brush shaft is rotationally mounted.
5. The toothbrush of claim 1, wherein the motor rotates at a speed of between 12,000 rpm and 18,000 rpm.
6. The toothbrush of claim 1, further comprising
   a first bearing receiving the brush shaft and positioned adjacent a first end of the brush shaft; and
   a second bearing receiving the brush shaft and positioned near a midpoint of the brush shaft.
7. The toothbrush of claim 6, further comprising an isolator damper substantially surrounding the brush shaft adjacent the first bearing to vibrationally isolate the linkage and the brush shaft from the handle.
8. The toothbrush of claim 1, wherein the eccentric pin includes a cam portion having a center of mass offset from the output axis.
9. The toothbrush of claim 8, wherein the cam portion includes a pivot axis offset from and parallel to the first axis of the eccentric pin.

10. The toothbrush of claim 1, wherein rotation of the eccentric pin by the motor causes the coupler to oscillate about an axis of the coupler.

11. The toothbrush of claim 1, wherein the brush shaft oscillates about a longitudinal axis of the brush shaft.

12. The toothbrush of claim 11, wherein the longitudinal axis of brush shaft is aligned with an axis parallel to, but offset from, the output axis.

13. A cleaning device providing oscillating motion comprising
   a handle member;
   a cleaning attachment connected to the handle member and having a plurality of cleaning members;
   a drive system housed within the handle member and having a drive axis;
   an output shaft housed within the handle member and having a distal end coupled to the cleaning attachment and a proximal end; and
   a coupling member having a first end coupled to the proximal end of the output shaft and a second end; and
   an eccentric member secured to the drive system and rotationally received within the second end of the coupling member, the eccentric member having a first portion axially aligned with the drive axis and a second portion axially offset from the drive axis.

14. The cleaning device of claim 13, wherein the drive axis is axially offset from a shaft axis of the output shaft.

15. The cleaning device of claim 13, wherein the output shaft oscillates between 200 and 300 cycles per second.

16. The cleaning device of claim 13, wherein the first portion of the eccentric member is secured to the drive system.

\* \* \* \* \*